United States Patent
Tu et al.

(10) Patent No.: US 11,622,740 B2
(45) Date of Patent: Apr. 11, 2023

(54) SYSTEMS AND METHODS FOR TAKING X-RAY IMAGES

(71) Applicant: SHANGHAI UNITED IMAGING HEALTHCARE CO., LTD., Shanghai (CN)

(72) Inventors: Jiali Tu, Shanghai (CN); Yongqin Xiao, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 90 days.

(21) Appl. No.: 17/105,627

(22) Filed: Nov. 26, 2020

(65) Prior Publication Data
US 2021/0077049 A1  Mar. 18, 2021

Related U.S. Application Data

(63) Continuation of application No. PCT/CN2019/088852, filed on May 28, 2019.

(30) Foreign Application Priority Data

May 28, 2018 (CN) .......................... 201810524687.7
May 28, 2018 (CN) .......................... 201810525560.7

(51) Int. Cl.
*A61B 6/00* (2006.01)
*A61B 6/04* (2006.01)
*A61B 6/08* (2006.01)

(52) U.S. Cl.
CPC .............. *A61B 6/5205* (2013.01); *A61B 6/04* (2013.01); *A61B 6/08* (2013.01); *A61B 6/40* (2013.01);
(Continued)

(58) Field of Classification Search
CPC .... A61B 6/04; A61B 6/08; A61B 6/40; A61B 6/42; A61B 6/4452; A61B 6/4464;
(Continued)

(56) References Cited

U.S. PATENT DOCUMENTS

2004/0264635 A1* 12/2004 Eberhard ............... A61B 6/025
378/22
2005/0232397 A1* 10/2005 Atzinger .................. A61B 6/08
378/163
(Continued)

FOREIGN PATENT DOCUMENTS

CN    101627917 A    1/2010
CN    102525524 A    7/2012
(Continued)

OTHER PUBLICATIONS

Translation of JP 2015217109 (Year: 2015).*
(Continued)

Primary Examiner — Dani Fox
Assistant Examiner — Soorena Kefayati
(74) Attorney, Agent, or Firm — Metis IP LLC

(57) ABSTRACT

The present disclosure relates to systems and methods for taking X-ray images. The method may include obtaining reference data associated with an object, the reference data including at least one of height data or historical data. The method may also include determining at least one of a start point or an end point of an imaging region associated with the object based on the reference data. The method may further include causing to take an X-ray image of the imaging region based on at least one of the start point or the end point.

18 Claims, 14 Drawing Sheets

(52) U.S. Cl.
CPC .............. *A61B 6/42* (2013.01); *A61B 6/463* (2013.01); *A61B 6/544* (2013.01); *A61B 6/545* (2013.01); *A61B 6/548* (2013.01); *A61B 6/56* (2013.01); *A61B 6/5241* (2013.01)

(58) Field of Classification Search
CPC ....... A61B 6/463; A61B 6/4476; A61B 6/487; A61B 6/5205; A61B 6/5235; A61B 6/5241; A61B 6/544; A61B 6/545; A61B 6/548; A61B 6/56
See application file for complete search history.

(56) References Cited

U.S. PATENT DOCUMENTS

| | | | |
|---|---|---|---|
| 2005/0279942 A1* | 12/2005 | Atzinger | A61B 6/5241 250/370.09 |
| 2006/0003121 A1* | 1/2006 | Scheller | B65D 65/40 428/35.2 |
| 2006/0034421 A1 | 2/2006 | Barkow et al. | |
| 2008/0152088 A1* | 6/2008 | Wang | H04N 5/32 378/98.12 |
| 2009/0245464 A1* | 10/2009 | Yamaguchi | A61B 6/5241 378/205 |
| 2010/0290707 A1* | 11/2010 | Wang | A61B 6/5241 378/62 |
| 2011/0150179 A1* | 6/2011 | Kato | A61B 6/588 250/370.08 |
| 2011/0188726 A1* | 8/2011 | Nathaniel | A61B 6/4441 378/42 |
| 2013/0058459 A1* | 3/2013 | Desaute | G21K 1/04 378/62 |
| 2013/0077744 A1* | 3/2013 | Kamiya | A61B 6/06 378/62 |
| 2013/0077765 A1* | 3/2013 | Welsh | A61B 6/4441 378/197 |
| 2013/0101088 A1* | 4/2013 | Fabrizio | A61B 6/08 378/205 |
| 2013/0148778 A1* | 6/2013 | Durgan | A61B 6/08 378/208 |
| 2015/0164440 A1* | 6/2015 | Rackow | A61B 5/7485 600/427 |
| 2015/0335305 A1* | 11/2015 | Moon | A61B 5/743 378/98.5 |
| 2016/0015331 A1* | 1/2016 | Wullenweber | A61B 5/7485 600/411 |
| 2016/0042012 A1* | 2/2016 | Lou | A61B 6/544 707/722 |
| 2016/0174930 A1* | 6/2016 | Braun | A61B 6/4417 378/205 |
| 2016/0247325 A1* | 8/2016 | Yu | A61B 6/5241 |
| 2016/0262714 A1* | 9/2016 | Krauss | A61B 6/544 |
| 2016/0278724 A1* | 9/2016 | Papaioannou | A61B 6/508 |
| 2017/0055925 A1* | 3/2017 | Lee | A61B 6/5241 |
| 2017/0055936 A1* | 3/2017 | Okuno | A61B 6/4452 |
| 2017/0135658 A1* | 5/2017 | Saito | A61B 6/5235 |
| 2018/0020994 A1* | 1/2018 | Yan | A61B 6/5235 378/4 |
| 2018/0184997 A1* | 7/2018 | Tsukagoshi | A61B 6/469 |
| 2018/0271462 A1* | 9/2018 | Shirota | A61B 6/461 |
| 2019/0130598 A1* | 5/2019 | Chikamatsu | A61B 6/0487 |
| 2019/0216414 A1* | 7/2019 | Inomata | A61B 6/5241 |
| 2019/0343479 A1* | 11/2019 | Sato | A61B 6/06 |

FOREIGN PATENT DOCUMENTS

| | | | |
|---|---|---|---|
| CN | 102783969 A | | 11/2012 |
| CN | 102805636 A | | 12/2012 |
| CN | 102908161 A | | 2/2013 |
| CN | 103284733 A | | 9/2013 |
| CN | 203777056 U | | 8/2014 |
| CN | 104287756 A | | 1/2015 |
| CN | 105615908 A | | 6/2016 |
| CN | 105686842 A | | 6/2016 |
| CN | 107456236 A | | 12/2017 |
| CN | 107468266 A | | 12/2017 |
| CN | 108652653 A | | 10/2018 |
| CN | 108670280 A | | 10/2018 |
| JP | 2012135371 A | | 7/2012 |
| JP | 2015217109 A | * | 12/2015 |
| JP | 2015217109 A | | 12/2015 |

OTHER PUBLICATIONS

English translation of JP2015217109 (Year: 2015).*
International Search Report in PCT/CN2019/088852 dated Sep. 2, 2019, 5 pages.
Written Opinion in PCT/CN2019/088852 dated Sep. 2, 2019, 5 pages.
The Extended European Search Report in European Application No. 19811376.3 dated May 28, 2021, 7 pages.

* cited by examiner

SYSTEMS AND METHODS FOR TAKING X-RAY IMAGES

CROSS-REFERENCE TO RELATED APPLICATIONS

This application is a continuation of International Application No. PCT/CN2019/088852, filed on May 28, 2019, which designates the United States of America and claims priority of Chinese Patent Application No. 201810525560.7 filed on May 28, 2018 and Chinese Patent Application No. 201810524687.7 filed on May 28, 2018, the contents of each of which are incorporated herein by reference in their entirety.

TECHNICAL FIELD

The present disclosure generally relates to medical field, and in particular, to systems and methods for medical imaging.

BACKGROUND

In medical field, medical imaging is an important means, which can provide significant reference information. For X-ray panoramic imaging, due to limited field of view, an X-ray imaging device acquires a plurality of intermediate images and determine a panoramic image of a body part (e.g., a spine, a lower limb) of a patient by stitching the plurality of intermediate images. Generally, a start point and an end point of an imaging region should be predefined and an imaging process may be executed based on the start point and the end point, during which a beam limiter may be used to indicate the imaging region. However, when a next imaging process is needed, the start point and/or the end point should be re-defined. Additionally, the use of the beam limiter may result in a relatively long imaging time and a relatively high error probability. Therefore, it is desirable to provide systems and methods for taking X-ray images efficiently and effectively.

SUMMARY

An aspect of the present disclosure relates to a medical imaging system for taking an X-ray panoramic image of an imaging part of an imaging object. The medical imaging system may include a support, an indicating device, a height measuring device, and a processor. The indicating device may be movably installed on the support. The height measuring device may be configured to obtain height data of the imaging object. The processor may communicatively connect with the indicating device and the height measuring device respectively, and be configured to control a movement of the indicating device based on the height data and information of the imaging part of the imaging object to determine an initial start point and an initial end point for taking the X-ray panoramic image.

In some embodiments, the system may further include a position modification device configured to modify positions of the initial start point and/or the initial end point to determine a modified start point and/or a modified end point for taking the X-ray panoramic image.

In some embodiments, the system may further include a wireless communication device configured to receive the height data obtained by the height measuring device and transmit a mobile control signal to the indicating device.

In some embodiments, the indicating device may include a laser indicating device.

In some embodiments, the laser indicating device may be installed on a back of the support relative to the imaging object.

In some embodiments, the laser indicating device may include a first laser indicating device and a second laser indicating device. The first laser indicating device may be configured to determine the start point for taking the X-ray panoramic image. The second laser indicating device may be configured to determine the end point for taking the X-ray panoramic image.

In some embodiments, the laser indicating device may include an emitting unit and a receiving unit, the receiving unit synchronously moving with the emitting unit and being at a same height with the emitting unit.

Another aspect of the present disclosure relates to a medical imaging method for taking an X-ray panoramic image of an imaging part of an imaging object according to the medical imaging system. The medical imaging method may include obtaining height data of the imaging object by using a height measuring device; determining an imaging region based on the height data and information of the imaging part of the imaging object; determining a start point and/or an end point for taking the X-ray panoramic image by controlling a movement of an indicating device based on the imaging region; and performing an X-ray panoramic imaging on the imaging part based on the start point and the end point.

In some embodiments, the medical imaging method may further include modifying a position of the indicating device to modify the start point and the end point for taking the X-ray panoramic image.

In some embodiments, the indicating device may include a first laser indicating device and a second laser indicating device. The medical imaging method may further include determining the start point for taking the X-ray panoramic image by controlling a movement of the first laser indicating device based on the imaging region and determining the end point for taking the X-ray panoramic image by controlling a movement of the second laser indicating device based on the imaging region.

A further aspect of the present disclosure relates to a medical imaging method applied to a medical imaging system for taking an X-ray panoramic image of an imaging part of an imaging object. The medical imaging method may include obtaining a start point and an end point for taking the X-ray panoramic image based on imaging records associated with the imaging part; performing a plurality of X-ray imaging operations on the imaging part based on the start point and the end point; and wherein the imaging records include historical data of panoramic imaging operations performed on the imaging part of the imaging object.

In some embodiments, the method may further include stitching a plurality of images obtained by the plurality of X-ray imaging operations to obtain an X-ray panoramic image of the imaging part.

In some embodiments, the method may further include obtaining an imaging region of the imaging part if there is no imaging record associated with the imaging part stored in the medical imaging system and determining the start point and the end point of the imaging part based on the imaging region.

In some embodiments, the method may further include storing the start point and the end point for taking the X-ray panoramic image of the imaging part as an imaging record associated with the imaging part in the medical imaging system.

In some embodiments, the method may further include performing a simulated imaging based on the start point and the end point and modifying the start point and the end point for taking the X-ray panoramic image if positions of the start point and the end point in the simulated imaging do not satisfy a preset condition.

In some embodiments, the method may further include obtaining the start point and the end point for taking the X-ray panoramic image automatically if a plurality of panoramic imaging operations under different positioning conditions are needed.

In some embodiments, the method may further include determining whether a next panoramic imaging under a next positioning condition is needed; obtaining the start point and the end point for taking the X-ray panoramic image automatically in response to determining that the next imaging under the next positioning condition is needed; and performing a plurality of X-ray imaging operations under the next positioning condition based on the start point and the end point.

A still further aspect of the present disclosure relates to a medical imaging device applied to a medical imaging system for taking an X-ray panoramic image of an imaging part of an imaging object. The medical imaging device may include a positioning module and an imaging module. The positioning module may be configured to obtain a start point and an end point for taking the X-ray panoramic image based on imaging records associated with the imaging part. The imaging module may be configured to perform a plurality of X-ray imaging operations on the imaging part based on the start point and the end point. The imaging records may include historical data of panoramic imaging operations performed on the imaging part of the object.

A still further aspect of the present disclosure relates to a medical imaging system including a storage, a processor, and a computer program stored in the storage and executed by the processor. When executing the computer program, the processor may implement the above method.

A still further aspect of the present disclosure relates to a computer readable storage medium storing a computer program thereon. When executing the computer program, a processor may implement the above method.

A still further aspect of the present disclosure relates to a method for taking X-ray images implemented on a computing device including a processor and a storage. The method may include obtaining reference data associated with an object, the reference data including at least one of height data or historical data; determining at least one of a start point or an end point of an imaging region associated with the object based on the reference data; and causing to take an X-ray image of the imaging region based on at least one of the start point or the end point.

In some embodiments, the method may further include obtaining the height data using a height measuring device.

In some embodiments, the method may further include transmitting a control signal associated with at least one of the start point or the end point to an indicating device, wherein the indicating device is to present at least one of the start point or the end point while taking the X-ray image.

In some embodiments, the indicating device may be movably installed on a support for carrying the imaging object.

In some embodiments, the indicating device may include a laser indicating device.

In some embodiments, the laser indicating device may include an emitting unit and a receiving unit, the receiving unit synchronously moving with the emitting unit and being at a same height with the emitting unit.

In some embodiments, the method may further include determining at least one of the start point or the end point of the imaging region based on the height data and a predetermined body part of the object.

In some embodiments, the method may further include determining whether the start point or the end point needs to be modified; determining a modified start point or a modified end point in response to determining that the start point or the end point needs to be modified; and causing to take the X-ray image of the imaging region based on at least one of the modified start point or the modified end point.

In some embodiments, the method may further include performing a simulated imaging based on the start point and the end point; determining whether the start point or the end point satisfies a preset condition based on a simulation result; and determining the modified start point or the modified end point in response to determining that the start point or the end point does not satisfy the preset condition.

In some embodiments, the method may further include capturing a plurality of intermediate images by performing a plurality of imaging operations within the start point and the end point and determining the X-ray image by stitching the plurality of intermediate images.

In some embodiments, the method may further include determining whether a next imaging under a next positioning condition is needed; obtaining the start point and the end point automatically in response to determining that the next imaging under the next positioning condition is needed; and performing the next imaging under the next positioning condition based on the start point and the end point.

In some embodiments, the X-ray image of the imaging region may be a panoramic image.

A still further aspect of the present disclosure relates to a system for X-ray imaging. The system may include a storage medium to store a set of instructions and a processor communicatively coupled to the storage medium. The system may execute the set of instructions to obtain reference data associated with an object, the reference data including at least one of height data or historical data; determine at least one of a start point or an end point of an imaging region associated with the object based on the reference data; and cause to take an X-ray image of the imaging region based on at least one of the start point or the end point.

In some embodiments, the system may further obtain the height data using a height measuring device.

In some embodiments, the system may further transmit a control signal associated with at least one of the start point or the end point to an indicating device, wherein the indicating device is to present at least one of the start point or the end point while taking the X-ray image.

In some embodiments, the indicating device may be movably installed on a support for carrying the imaging object.

In some embodiments, the indicating device may include a laser indicating device.

In some embodiments, the laser indicating device may include an emitting unit and a receiving unit, the receiving unit synchronously moving with the emitting unit and being at a same height with the emitting unit.

In some embodiments, the system may determine at least one of the start point or the end point of the imaging region based on the height data and a predetermined body part of the object.

In some embodiments, the system may determine whether the start point or the end point needs to be modified. The system may determine a modified start point or a modified end point in response to determining that the start point or the end point needs to be modified. The system may cause to take the X-ray image of the imaging region based on at least one of the modified start point or the modified end point.

In some embodiments, the system may perform a simulated imaging based on the start point and the end point. The system may determine whether the start point or the end point satisfies a preset condition based on a simulation result. The system may determine the modified start point or the modified end point in response to determining that the start point or the end point does not satisfy the preset condition.

In some embodiments, the system may capture a plurality of intermediate images by performing a plurality of imaging operations within the start point and the end point. The system may determine the X-ray image by stitching the plurality of intermediate images.

In some embodiments, the system may determine whether a next imaging under a next positioning condition is needed. The system may obtain the start point and the end point automatically in response to determining that the next imaging under the next positioning condition is needed. The system may perform the next imaging under the next positioning condition based on the start point and the end point.

In some embodiments, the X-ray image of the imaging region may be a panoramic image.

A still further aspect of the present disclosure relates to a system for X-ray imaging. The system may include an obtaining module, a determination module, and an imaging module. The obtaining module may be configured to obtain reference data associated with an object, the reference data including at least one of height data or historical data. The determination module may be configured to determine at least one of a start point or an end point of an imaging region associated with the object based on the reference data. The imaging module may be configured to cause to take an X-ray image of the imaging region based on at least one of the start point or the end point.

In some embodiments, the obtaining module may be further configured to obtain the height data using a height measuring device.

In some embodiments, the imaging module may be further configured to transmit a control signal associated with at least one of the start point or the end point to an indicating device, wherein the indicating device is to present at least one of the start point or the end point while taking the X-ray image.

In some embodiments, the indicating device may be movably installed on a support for carrying the imaging object.

In some embodiments, the indicating device may include a laser indicating device.

In some embodiments, the laser indicating device may include an emitting unit and a receiving unit, the receiving unit synchronously moving with the emitting unit and being at a same height with the emitting unit.

In some embodiments, the determination module may be further configured to determine at least one of the start point or the end point of the imaging region based on the height data and a predetermined body part of the object.

In some embodiments, the determination module may be further configured to determine whether the start point or the end point needs to be modified and determine a modified start point or a modified end point in response to determining that the start point or the end point needs to be modified. The imaging module may be further configured to cause to take the X-ray image of the imaging region based on at least one of the modified start point or the modified end point.

In some embodiments, the imaging module may be further configured to perform a simulated imaging based on the start point and the end point. The determination module may be further configured to determine whether the start point or the end point satisfies a preset condition based on a simulation result and determine the modified start point or the modified end point in response to determining that the start point or the end point does not satisfy the preset condition.

In some embodiments, the imaging module may be further configured to capture a plurality of intermediate images by performing a plurality of imaging operations within the start point and the end point and determine the X-ray image by stitching the plurality of intermediate images.

In some embodiments, the determination module may be further configured to determine whether a next imaging under a next positioning condition is needed and obtain the start point and the end point automatically in response to determining that the next imaging under the next positioning condition is needed. The imaging module may be further configured to perform the next imaging under the next positioning condition based on the start point and the end point.

In some embodiments, the X-ray image of the imaging region may be a panoramic image.

A still further aspect of the present disclosure relates to a non-transitory computer readable medium including executable instructions. When the executable instructions are executed by at least one processor, the executable instructions may direct the at least one processor to perform a method. The method may include obtaining reference data associated with an object, the reference data including at least one of height data or historical data; determining at least one of a start point or an end point of an imaging region associated with the object based on the reference data; and causing to take an X-ray image of the imaging region based on at least one of the start point or the end point.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1:
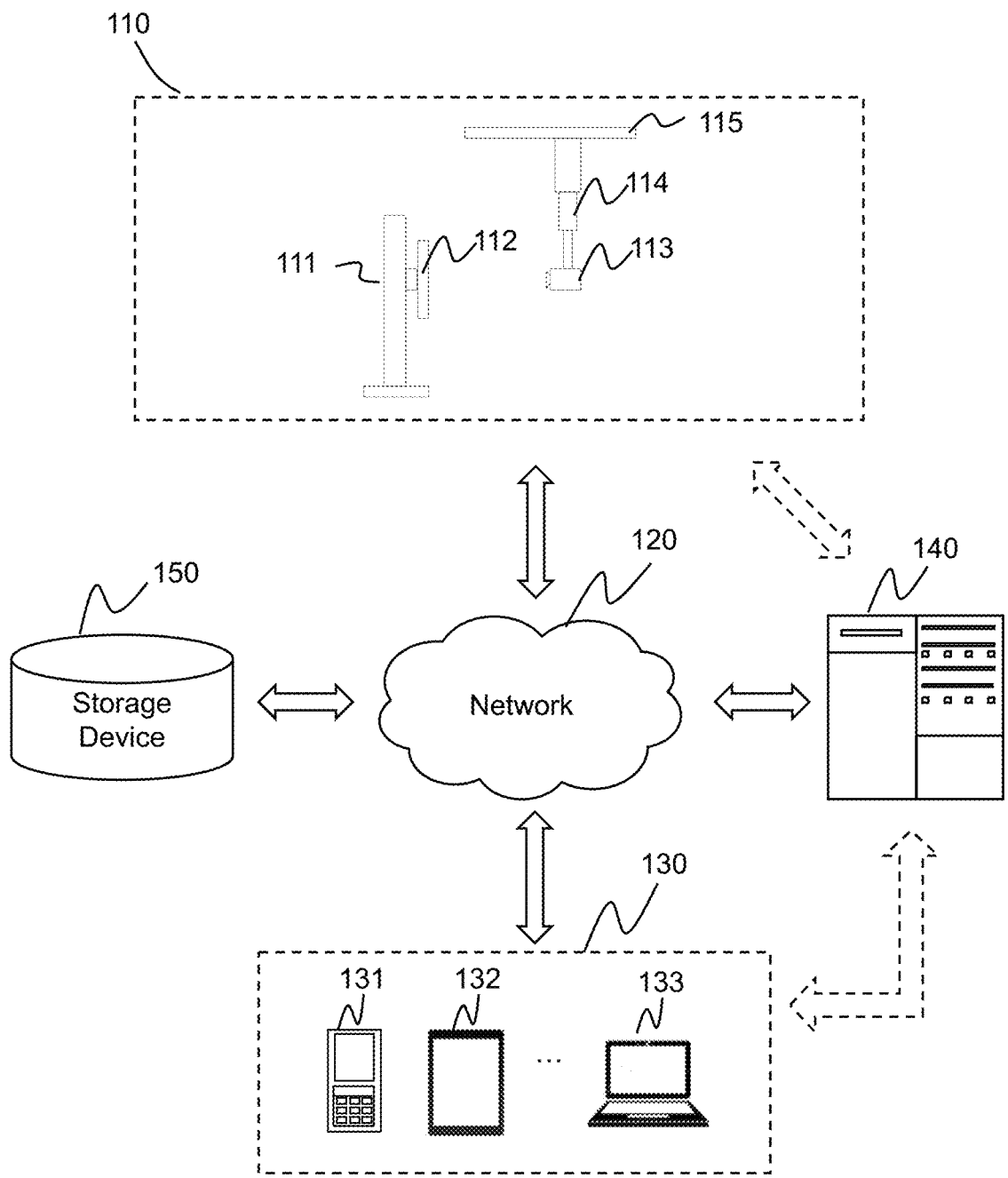
FIG. 1 is a schematic diagram illustrating an exemplary X-ray imaging system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this disclosure, specify the presence of stated features, integers, steps, operations, elements, and/or components, but do not preclude the presence or addition of one or more other features, integers, steps, operations, elements, components, and/or groups thereof.

It will be understood that the terms "system," "engine," "unit," "module," and/or "block" used herein are one method to distinguish different components, elements, parts, sections, or assemblies of different levels in ascending order. However, the terms may be displaced by another expression if they achieve the same purpose.

Generally, the words "module," "unit," or "block," used herein refer to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for performing on computing devices (e.g., processor 210 illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to performing). Such software code may be stored, partially or fully, on a storage device of the performing computing device, for performing by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to" another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood, the operations of the flowcharts may be implemented not in order. Conversely, the operations may be implemented in inverted order, or simultaneously. Moreover, one or more other operations may be added to the flowcharts. One or more operations may be removed from the flowcharts.

An aspect of the present disclosure relates to systems and methods for taking X-ray images. The systems may obtain reference data associated with an object (e.g., a patient). The reference data may include height data (e.g., a height of the patient), historical data (e.g., imaging records of the patient), etc. The systems may obtain the height data from a height measuring device (e.g., an infrared measuring device, an ultrasonic measuring device) or obtain the historical data from a storage device. The systems may determine at least one of a start point or an end point of an imaging region associated with the object based on the reference data. The systems may further take an X-ray image (e.g., a panoramic image) of the imaging region based on at least one of the start point or the end point. For example, the systems may capture a plurality of intermediate images within the start point and the end point and determine the X-ray image by stitching the plurality of intermediate image. According to the systems and methods of the present disclosure, the start point and/or the end point are determined based on the height data or historical data, thereby improving the efficiency of the imaging process.

FIG. 1 is a schematic diagram illustrating an exemplary X-ray imaging system according to some embodiments of the present disclosure. As shown in FIG. 1, the X-ray imaging system 100 may include an acquisition device 110, a network 120, a terminal device 130, a processing device 140, and a storage device 150. The components of the X-ray imaging system 100 may be connected in one or more of various ways. Merely by way of example, the acquisition device 110 may be connected to the processing device 140 through the network 120. As another example, the acquisition device 110 may be connected to the processing device 140 directly as indicated by the bi-directional arrow in dotted lines linking the acquisition device 110 and the processing device 140. As still another example, the storage device 150 may be connected to the processing device 140 directly or through the network 120. As still another example, the terminal device 130 may be connected to the processing device 140 directly (as indicated by the bi-directional arrow in dotted lines linking the terminal device 130 and the processing device 140) or through the network 120.

The acquisition device 110 may be configured to scan an object (e.g., a patient) using X-rays and generate image data associated with the object. In some embodiments, the object to be imaged may include a body, substance, or the like, or any combination thereof. In some embodiments, the object may include a specific portion of a body, such as a head, a thorax, an abdomen, a lower limb, a spine, or the like, or any combination thereof. In some embodiments, the object may include a specific organ, such as a breast, an esophagus, a trachea, a bronchus, a stomach, a gallbladder, a small intestine, a colon, a bladder, a ureter, a uterus, a fallopian tube, etc. In the present disclosure, "object" and "subject" are used interchangeably.

Merely by way of example, the acquisition device 110 may be a suspended X-ray imaging device including a column 111, a detector 112 (e.g., a flat panel detector), a rail 115, a suspension holder 114, and an X-ray generator 113. The column 111 may be configured to support the detector 112. In some embodiments, the column 111 may have a column-shape illustrated in FIG. 1. Alternatively, the column 111 may have any other shape, such as a C-shape, an O-shape, a U-shape, a G-shape, or the like, or a combination thereof. The suspension holder 114 may be configured to suspend the X-ray generator 113 on the rail 115 or on a wall. In some embodiments, the suspension holder 114 may be movable and may move along the rail 115, during which the X-ray generator 113 may move with the suspension holder 114. The X-ray generator 113 may include a bulb (not shown in FIG. 1) and emit X-rays to the object through the bulb. The detector 112 may be configured to receive X-rays emitted from the X-ray generator 113 passing through the object. In some embodiments, the detector 112 may also be configured to perform an imaging operation to obtain an image based on the X-rays received from the X-ray generator 113. More descriptions of the acquisition device 110 may be found elsewhere in the present disclosure (e.g., FIG. 4 and the description thereof).

In some embodiments, the acquisition device 110 may transmit the image data to the processing device 140 for further processing. In some embodiments, the acquisition device 110 may transmit the image data to the storage device 150 to be stored.

The network 120 may include any suitable network that can facilitate exchange of information and/or data for the X-ray imaging system 100. In some embodiments, one or more components (e.g., the acquisition device 110, the terminal device 130, the processing device 140, the storage device 150) of the X-ray imaging system 100 may communicate information and/or data with one or more other components of the X-ray imaging system 100 via the network 120. For example, the processing device 140 may obtain one or more instructions from the terminal device 130 via the network 120. As another example, the processing device 140 may obtain image data from the acquisition device 110 or the storage device 150 via the network 120. The network 120 may be and/or include a public network (e.g., the Internet), a private network (e.g., a local area network (LAN), a wide area network (WAN))), a wired network (e.g., an Ethernet network), a wireless network (e.g., an 802.11 network, a Wi-Fi network,), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the X-ray imaging system 100 may be connected to the network 120 to exchange data and/or information.

The terminal device 130 may enable interactions between a user and the X-ray imaging system 100. The terminal device 130 may include a mobile device 131, a tablet computer 132, a laptop computer 133, or the like, or any combination thereof. In some embodiments, the mobile device 131 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 130 may be part of the processing device 140.

Figure 2:
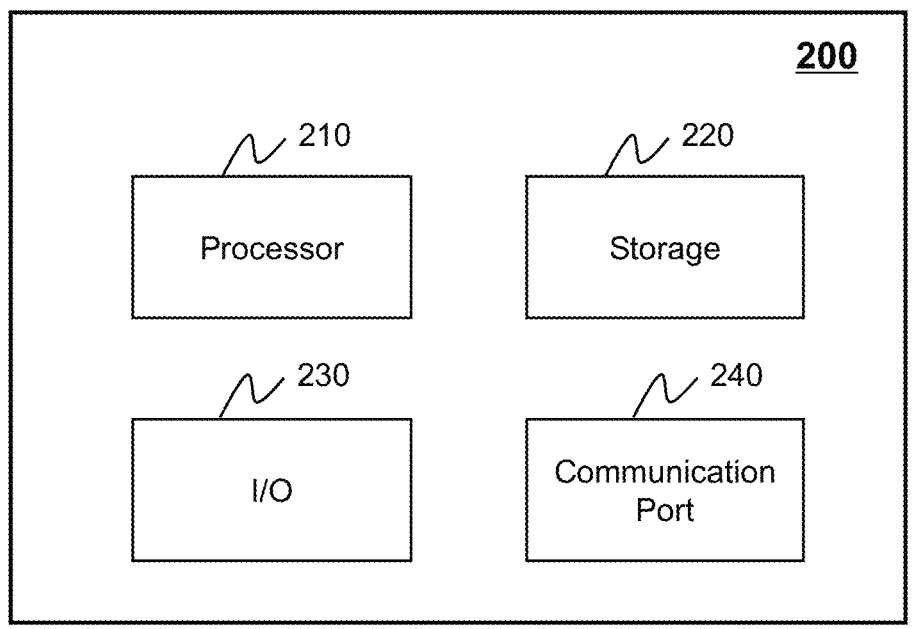
FIG. 2 is a schematic diagram illustrating exemplary hardware and/or software components of an exemplary computing device according to some embodiments of the present disclosure.

The processing device 140 may process data and/or information obtained from the acquisition device 110, the terminal device 130, and/or the storage device 150. For example, the processing device 140 may obtain imaging records associated with an object and perform an X-ray imaging based on a start point and/or an end point in the imaging records. As another example, the processing device 140 may obtain height data associated with the object, determine a start point and/or an end point based on the height data, and perform the X-ray imaging based on the start point and/or the end point. In some embodiments, the processing device 140 may be a computer, a user console, a single server or a server group, etc. The server group may be centralized or distributed. In some embodiments, the processing device 140 may be local or remote. For example, the processing device 140 may access information and/or data stored in the acquisition device 110, the terminal device 130, and/or the storage device 150 via the network 120. As another example, the processing device 140 may be directly connected to the acquisition device 110, the terminal device 130, and/or the storage device 150 to access stored information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented by a computing device 200 including one or more components as illustrated in FIG. 2. In some embodiments, the processing device 140 or a portion of the processing device 140 may be integrated into the acquisition device 110.

The storage device 150 may store data, instructions, and/or any other information. In some embodiments, the storage device 150 may store data obtained from the acquisition device 110, the terminal device 130 and/or the processing device 140. In some embodiments, the storage device 150 may store data and/or instructions that the processing device 140 may execute or use to perform exemplary methods described in the present disclosure. In some embodiments, the storage device 150 may include a mass storage device, a removable storage device, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more other components (e.g., the processing device 140, the terminal device 130) of the X-ray imaging system 100. One or more components of the X-ray imaging system 100 may access the data or instructions stored in the storage device 150 via the network 120. In some embodiments, the storage device 150 may be directly connected to or communicate with one or more other components (e.g., the processing device 140, the terminal device 130) of the X-ray imaging system 100. In some embodiments, the storage device 150 may be part of the processing device 140.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, the installation mode of the X-ray generator 113 is not limited to the suspension mode, other installation modes such as a console mode are also applicable to the X-ray imaging system 100.

FIG. 2 is a schematic diagram illustrating exemplary hardware and/or software components of an exemplary computing device according to some embodiments of the present disclosure. In some embodiments, the processing device 140 may be implemented on the computing device 200. As illustrated in FIG. 2, the computing device 200 may include a processor 210, a storage 220, an input/output (I/O) 230, and a communication port 240.

The processor 210 may execute computer instructions (e.g., program code) and perform functions of the processing device 140 in accordance with techniques described herein. The computer instructions may include, for example, routines, programs, objects, components, data structures, procedures, modules, and functions, which perform particular functions described herein. For example, the processor 210 may process image data obtained from the acquisition device 110, the terminal device 130, the storage device 150, and/or any other component of the X-ray imaging system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the acquisition device 110, the terminal device 130, the storage device 150, and/or any other component of the X-ray imaging system 100. In some embodiments, the storage 220 may include a mass storage device, a removable storage device, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. The storage 220 may be similar to the storage device 150 described in connection with FIG. 1.

The I/O 230 may input and/or output signals, data, information, etc. In some embodiments, the I/O 230 may enable a user interaction with the processing device 140. In some embodiments, the I/O 230 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 240 may be connected to a network (e.g., the network 120) to facilitate data communications. The communication port 240 may establish connections between the processing device 140 and the acquisition device 110, the terminal device 130, and/or the storage device 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
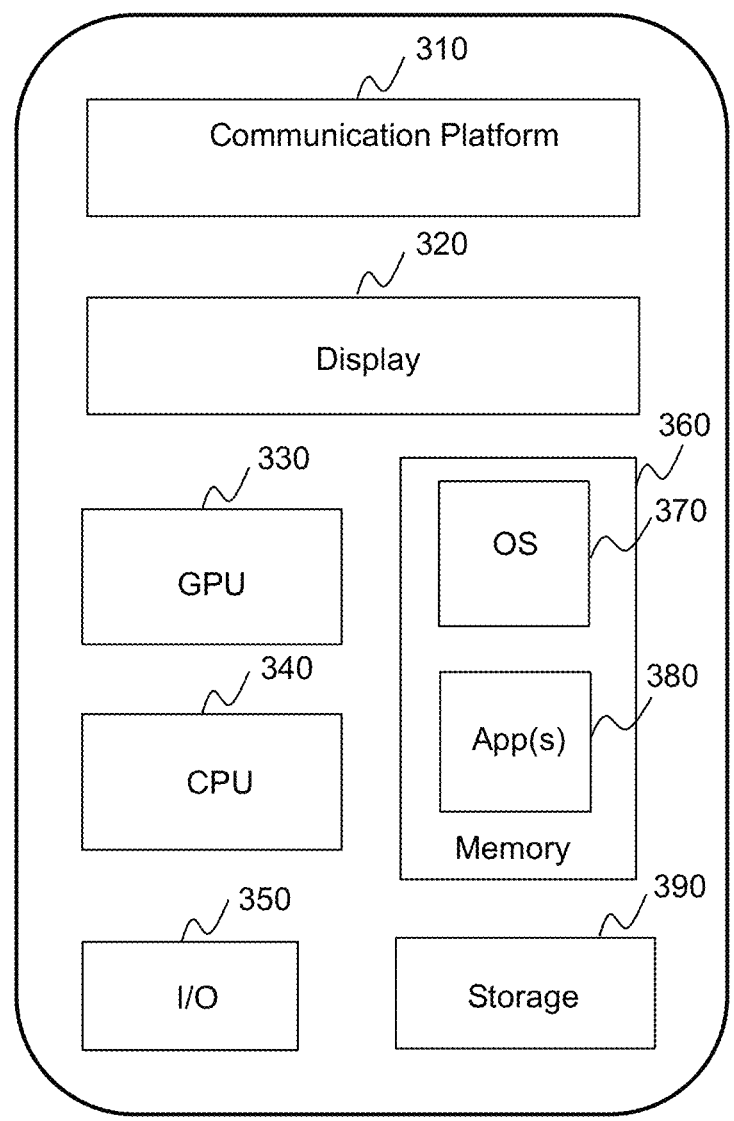
FIG. 3 is a schematic diagram illustrating exemplary hardware and/or software components of an exemplary mobile device according to some embodiments of the present disclosure.

FIG. 3 is a schematic diagram illustrating exemplary hardware and/or software components of an exemplary mobile device according to some embodiments of the present disclosure. In some embodiments, the terminal device 130 may be implemented on the mobile device 300. As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the X-ray imaging system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
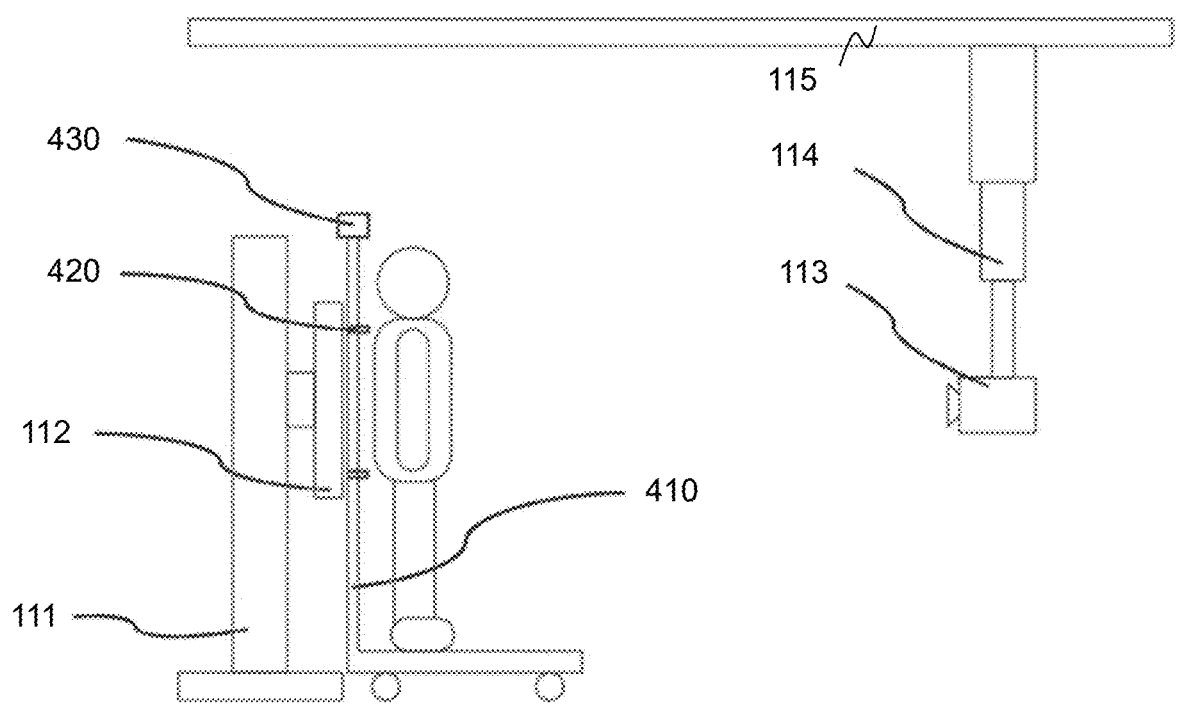
FIG. 4 is a schematic diagram illustrating an exemplary medical imaging system according to some embodiments of the present disclosure.

FIG. 4 is a schematic diagram illustrating an exemplary medical imaging system according to some embodiments of the present disclosure. In some embodiments, the medical imaging system 400 may be used for taking an X-ray panoramic image of an imaging part of an imaging object (also referred to as an "object").

As illustrated in FIG. 4, in addition to the components of the acquisition device 110 illustrated in FIG. 1, the medical imaging system 400 may also include a support 410, an indicating device 420, a height measuring device 430, and a processor (e.g., the processor 210) (not shown in FIG. 4). The indicating device 420 may be movably installed on the support 410. The height measuring device 430 may be configured to obtain height data of the imaging object. Specifically, the height measuring device 430 may be, for example, an infrared measuring device, an ultrasonic measuring device, or any other measuring device well known in the art. The processor may be communicatively connected with the height measuring device 430 and the indicating device 420 respectively, and may be configured to control a movement of the indicating device 420 based on the height data and information associated with the imaging part and determine an initial start point and/or an initial end point for taking the X-ray panoramic image.

Specifically, the support 410 may be an L-type support including a baseboard and a backboard. The baseboard may be configured to carry the imaging object and the indicating device 420 may be movably (e.g., movably up and down) installed on the backboard. The indicating device 420 may indicate a start point and/or an end point for taking the X-ray panoramic image. The height measuring device 430 may be installed on the support 410 or any other location that is convenient for measuring the height of the imaging object. The support 410 may directly face the X-ray generator 113 and a back of the support 410 may cling to the detector 112 which is movably install on the column 111.

Further, during a process for taking an X-ray panoramic image of the imaging part of the imaging object, the imaging object stands on the support 410 and the height measuring device 430 measures the height data of the imaging object and transmits the height data to the processor. Since a specific body part (e.g., a lower limb) of a human body corresponds to a generally specific range (e.g., ⅓ part of a range from feet to waist) on the human body, the processor can determine an imaging region based on the obtained height data and information of the imaging part of the imaging object, thereby controlling the indicating device 420 to move to the initial start point and/or the initial end point for taking the X-ray panoramic image. A doctor or an operator may determine whether the initial start point and/or the initial end point satisfy imaging needs. If the initial start point and/or the initial end point satisfy the imaging needs, the X-ray image (also referred to as an "X-ray panoramic image") of the imaging object may be taken based on the initial start point and/or the initial end point. If the initial start point and/or the initial end point does not satisfy the imaging needs, positions of the initial start point and/or the initial end point may be modified. It should be understood that the positions of the initial start point and/or the initial end point may be manually modified by the doctor or the operator through adjusting the indicating device 420, or may be automatically modified by, for example, a position modification device (not shown).

A projection range of X-rays emitted (i.e., an imaging range of the X-ray generator 113) by the X-ray generator 113 at various positions on the detector 112 may be determined based on a height of the indicating device 420 and a distance between the detector 112 and a plane where the X-ray generator 113 is located. Further, a first setting position of the X-ray generator 113 may be determined when an upper limit of the imaging range reaches the initial start point and a second setting position of the X-ray generator 113 may be determined when a lower limit of the imaging range reaches the initial end point.

An angle of the X-ray generator 113 or a length of the suspension holder 114 may be adjusted based on the first setting position of the X-ray generator 113, then the upper limit of the imaging range of the X-ray generator 113 reaches the initial start point. A bulb in the X-ray generator 113 may emit X-rays and the detector 112 may receive X-rays passing through the imaging object for taking a first image (also referred to as a "first intermediate image"). After the first image is taken, a target position for taking a second image may be determined by continuously adjusting the angle of the X-ray generator 113 and/or the length of the suspension holder 114. Further, the detector 112 may synchronously move to the target position for taking a second image. A plurality of images may be taken by repeating the above X-ray imaging operation (also referred to as an "intermediate imaging operation") until the X-ray generator 113 reaches the second setting position and the lower limit of the imaging range reaches the end point. During the whole imaging process, images (i.e., intermediate images) obtained in any two adjacent consecutive imaging operations may have a same overlapping region to facilitate a subsequent operation for stitching the intermediate images. After the imaging of the imaging part is completed, the plurality of intermediate images obtained by the plurality of X-ray imaging operations may be stitched to obtain an X-ray panoramic image of the imaging part.

According to the medical imaging system, an imaging region for taking an X-ray panoramic image may be determined based on height data of a patient and a start point and/or an end point of the imaging region may be indicated on the support, which can provide an accurate positing of the start point and/or the end point for taking the X-ray panoramic image, and is easy to adjust and operate without a beam limiter, thereby reducing additional harm to the patient.

In some embodiments, the medical imaging system 400 may further include a position modification device configured to modify positions of the initial start point and/or the initial end point to determine a modified start point and/or a modified end point for taking the X-ray panoramic image.

Specifically, since different persons correspond to different heights and different figures, there may be an error between the imaging region that is determined based on the height data and an actual imaging region. In order to reduce the error, the medical imaging system 400 may include a position modification device. After the indicating device 420 is controlled to move to the initial start point and/or the initial end point for taking the X-ray image, a doctor or an operator may determine whether the initial start point and/or the initial end point need to be modified based on the actual imaging region. If the initial start point and/or the initial end point need to be modified, the position of the indicating device 420 may be modified by the position modification device to determine a modified start point and/or a modified end point for taking the X-ray panoramic image. Further, the X-ray panoramic image may be taken based on the modified start point and/or the modified end point, which can make the imaging more accurately.

In some embodiments, the medical imaging system 400 may further include a wireless communication device configured to receive the height data obtained by the height measuring device 430 and transmit a mobile control signal (also referred to as a "control signal") to the indicating device 420 via, for example, a wireless communication (e.g., the network 120).

Specifically, the processor may be communicatively connected with the indicating device 420 and the height measuring device 430 via a wireless mode. The wireless communication device may transmit the mobile control signal from the processor to the indicating device 420 and transmit the position information of the indicating device 420 to the processor. Therefore, the doctor or the operator may obtain and control the position of the indicating device 420 and modify the position of the indicating device 420 when the initial start point and/or the initial end point need to be modified. By using the wireless communication device, an influence of wires on the movement of the indicating device 420 and/or the X-ray imaging can be avoided, the positions of the height measuring device 430 and the processor can be set more flexibly, and the doctor can operate the X-ray imaging remotely, thereby reducing the damage caused by X-rays.

In some embodiments, the indicating device 420 in the medical imaging system 400 may include a laser indicating device.

Specifically, the indicating device 420 may be a laser indicating device which may indicate the imaging region by emitting a laser. Compared with an indicating manner in which the start point and/or the end point are indicated by a mechanical device such as a ruler, an indicating manner in which the start point and/or the end point are indicated by the laser indicating device is more intuitive, accurate, and easy to observe. Further, the laser indicating device is generally smaller in size, therefore, it may be flexible for setting, easy for adjusting, and not easily damaged. However, the present disclosure does not exclude the use of the mechanical device such as the ruler to indicate the start point and/or end point for taking the X-ray image. If the mechanical device such as the ruler is used, a transmission mechanism is needed to move up and down and stop at a predetermined position based on instructions sent by the processor, which is easy to implement.

In some embodiments, the laser indicating device may be installed on a back of the support 410 relative to the imaging object.

Specifically, the imaging object (e.g., a patient) stands on the front of the support 410 and the laser indicating device is installed on the back of the support 410, which can effectively avoid a situation in which the imaging object stands too close to the backboard of the support 410 to block an optical path of the laser indicating device, and can avoid a possibility of laser accidental injury to the body of the imaging object. Moreover, the backboard of the support 410 may be made of a transparent material such as glass so that the laser indicating device can be embedded in the support 410. Further, the transparent backboard of the support 410 also can reduce the obstruction and scattering of X-rays, and improve the imaging quality for taking the X-ray image.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

Figure 5:
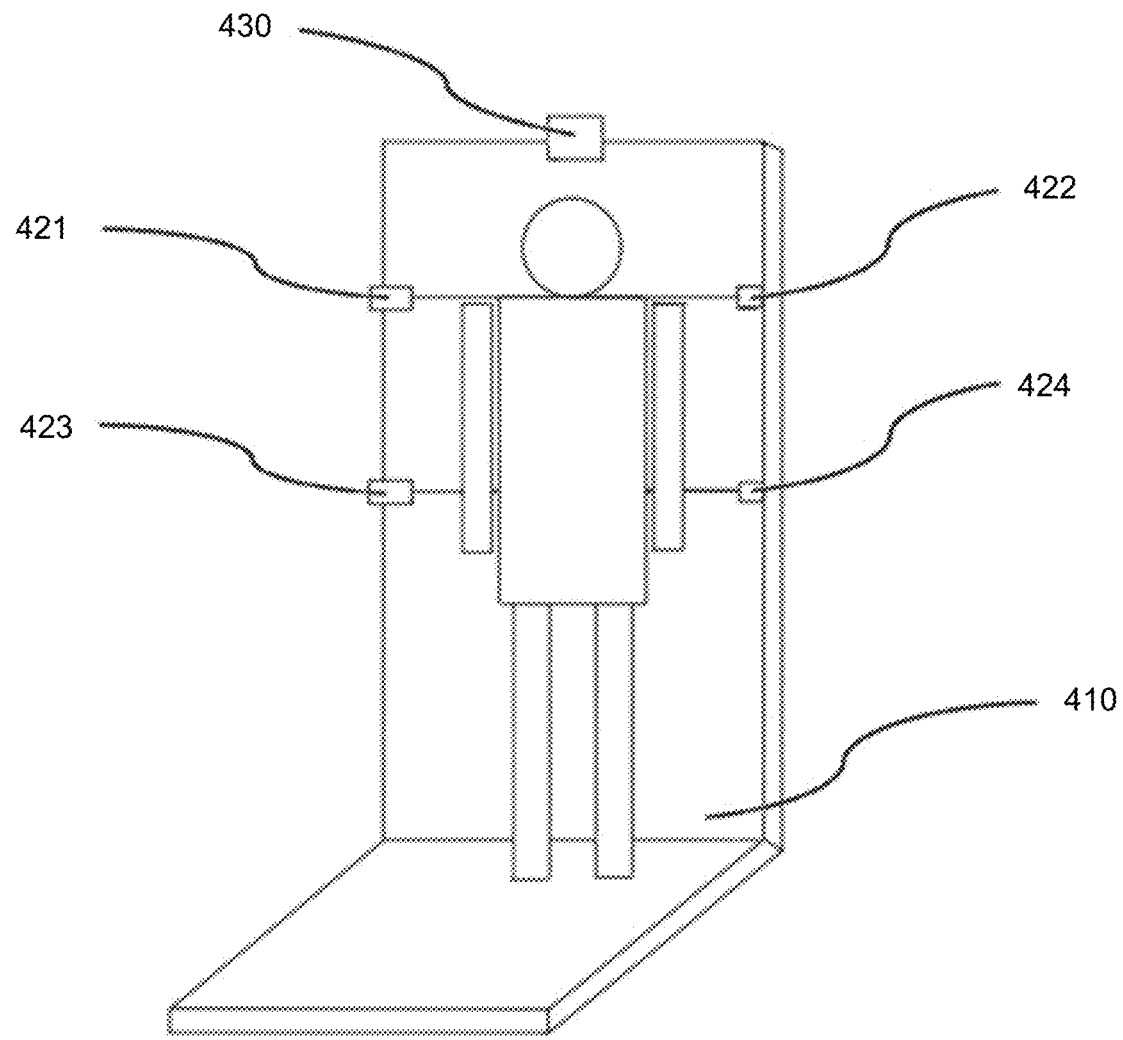
FIG. 5 is a schematic diagram illustrating an exemplary local structure of an exemplary medical imaging system according to some embodiments of the present disclosure.

FIG. 5 is a schematic diagram illustrating an exemplary local structure of an exemplary medical imaging system according to some embodiments of the present disclosure. In some embodiments, the laser indicating device may include a first laser indicating device and a second laser indicating device. The first laser indicating device may be configured to determine the start point for taking the X-ray panoramic image and the second laser indicating device may be configured to determine the end point for taking the X-ray panoramic image. Each laser indicating device may include an emitting unit and a receiving unit, wherein the receiving unit may synchronously move with the emitting unit and may be at a same height with the emitting unit.

Specifically, the indicating device 420 may include a first laser emitting unit 421, a first laser receiving unit 422, a second laser emitting unit 423, and a second laser receiving unit 424. The first laser emitting unit 421 and the first laser receiving unit 422 form the first laser indicating device which is configured to determine the start point for taking the X-ray panoramic image. The second laser emitting unit 423 and the second laser receiving unit 424 form the second laser indicating device which is configured to determine the end point for taking the X-ray panoramic image. The processor may control the first laser emitting unit 421 and the second laser emitting unit 423 to move to the start point and the end point for taking the X-ray panoramic image respectively. The first laser receiving unit 422 and the second laser receiving unit 424 may automatically follow a corresponding laser emitting unit and synchronously move with the corresponding laser emitting unit, and may be at a same height with the corresponding emitting unit and parallel to the baseboard of the support 410, thereby making the laser indicating of the start point and/or the end point is clearer and more accurate.

Figure 6:
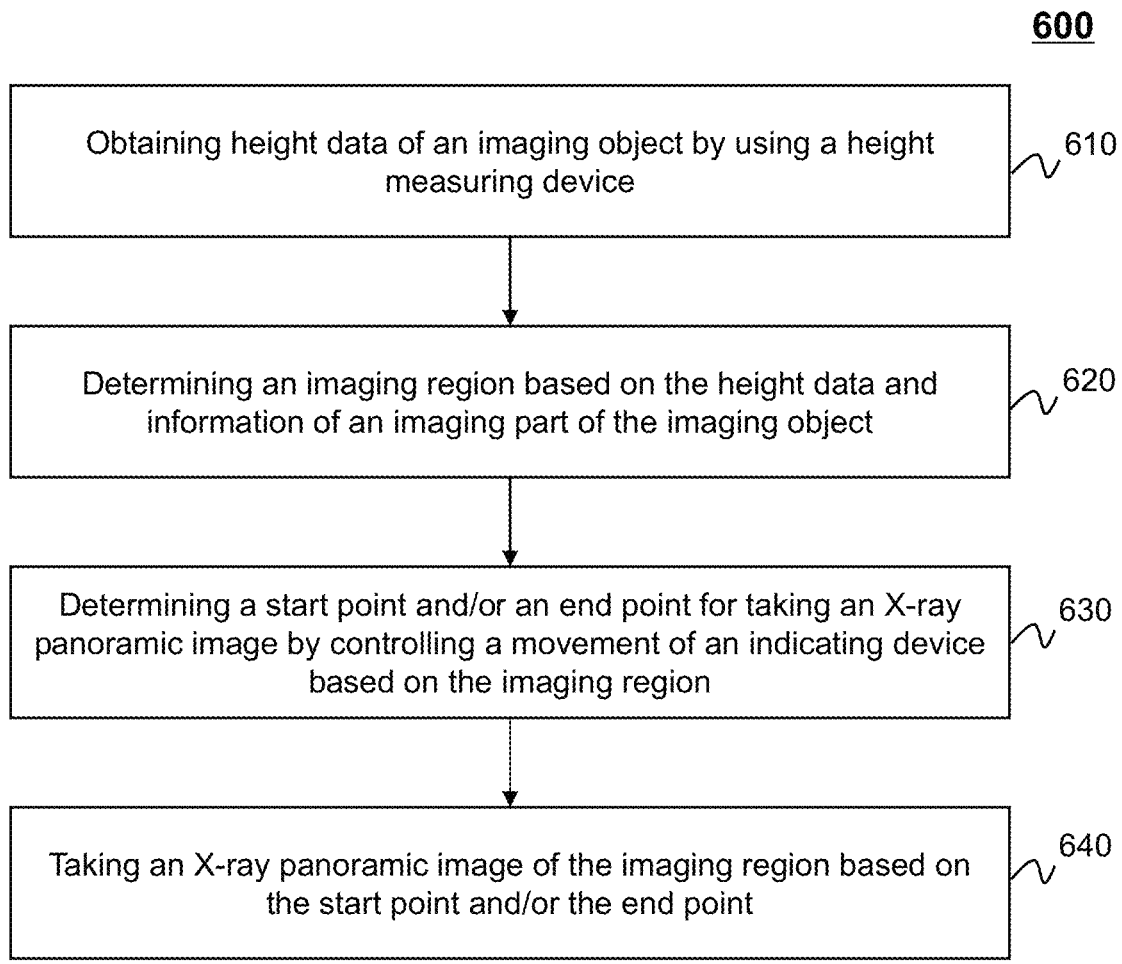
FIG. 6 is a flowchart illustrating an exemplary process for taking a medical image according to some embodiments of the present disclosure.

FIG. 6 is a flowchart illustrating an exemplary process for taking a medical image according to some embodiments of the present disclosure. In some embodiments, at least part of process 600 may be performed by the processing device 140 (implemented in, for example, the computing device 200 shown in FIG. 2). For example, the process 600 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, or one or more modules illustrated in FIG. 12 or FIG. 13). The operations of the illustrated process presented below are intended to be illustrative. In some embodiments, the process 600 may be accomplished with one or more additional operations not described, and/or without one or more of the operations discussed. Additionally, the order in which the operations of the process 600 as illustrated in FIG. 6 and described below is not intended to be limiting.

In 610, height data of an imaging object may be obtained by using a height measuring device (e.g., the height measuring device 430). The height data of the imaging object may be obtained by the processing device 140 (e.g., an obtaining module 1310 illustrated in FIG. 13) from the height measuring device.

Specifically, during a process for taking an X-ray panoramic image of an imaging part of the imaging object, the height measuring device may measure a height of the imaging object. The height measuring device may be installed on the support 410 or any other location that is convenient for measuring the height of the imaging object. The obtained height data of the imaging object may be transmitted to the processor after the measurement is completed.

In 620, an imaging region may be determined based on the height data and information of the imaging part of the imaging object. The imaging region may be determined by the processing device 140 (e.g., a determination module 1320 illustrated in FIG. 13).

Specifically, after receiving the height data of the imaging object, the processor may determine the imaging region based on the height data and information of the imaging part of the imaging object. The information of the imaging part of the imaging object may be automatically obtained based on medical records of the imaging object or manually input by a doctor or an operator.

Further, a relationship between "height" and "imaging part" may be expressed by a mathematical expression. For example, a relationship between a body part (e.g., a chest, an upper abdomen, a lower abdomen, a spine, a lower limb) and a height L may be input in advance based on a mathematical expression obtained through experience. For example, a relationship between the chest and the height L may be defined as L*a~L*b based on experience. Alternatively, the relationship between "height" and "imaging part" may be defined by big data. For example, mass data including height data of men and women with various features (e.g., age, native place, medical history) and data of various body parts may be collected. According to the mass data, a relationship among the height and various body parts may be obtained, even a relationship among men and women with various features may also be obtained. Further, the relationship may be stored in a memory (e.g., the storage device 150, the storage 220, the storage 390) to be further used by the processor when implementing the method of the present disclosure.

In 630, a start point and/or an end point for taking the X-ray panoramic image may be determined by controlling a movement of an indicating device (e.g., the indicating device 420) based on the imaging region. The start point and/or the end point for taking the X-ray panoramic image may be determined by the processing device 140 (e.g., the determination module 1320 illustrated in FIG. 13).

Specifically, after determining the imaging region, the processor may control the indicating device to move on the backboard of the support 410 to a target height of the start point and/or the end point for taking the X-ray image based on the imaging region. The indicating device may be a laser device configured to indicate the start point and/or the end point for taking the X-ray image by a laser. The indicating device may also be a mechanical device such as a ruler which can clearly and accurately indicate the start point and/or the end point for taking the X-ray image. The start point and/or the end point may be successively indicated by a single indicating device in the process for determining the start point and/or the end point. The start point and/or the end point may also be indicated by two indicating devices respectively. A doctor or an operator may determine whether the start point and/or the end point satisfy imaging needs after the indicating device moves to the start point and/or the end point. If the start point and/or the end point satisfy the imaging needs, the doctor or the operator may confirm the start point and/or the end point. If the start point and/or the end point does not satisfy the imaging needs, the start point and/or the end point may be modified to determine a modified start point and/or a modified end point for taking the X-ray image.

In 640, an X-ray panoramic image of the imaging region may be taken based on the start point and/or the end point. The X-ray panoramic image of the imaging region may be taken by the acquisition device 110 or by the processing device 140 (e.g., an imaging module 1330 illustrated in FIG. 13).

Specifically, after the start point and/or the end point are determined, the X-ray generator 113 and the detector 112 may be controlled to capture a plurality of images by performing a plurality of imaging operations from the start point to the end point. The plurality of images may be stitched to determine an X-ray panoramic image of imaging part.

According to the medical imaging method, an imaging region for taking an X-ray panoramic image may be determined based on height data of a patient and a start point and/or an end point of the imaging region may be indicated on the support, which can provide an accurate positing of the start point and/or the end point for taking the X-ray panoramic image, and is easy to adjust and operate without a beam limiter, thereby reducing additional harm to the patient.

In some embodiments, a position of the indicating device may be modified by the position modification device to determine a modified start point and/or a modified end point for taking the X-ray panoramic image before operation 640.

Specifically, a doctor or an operator may determine whether the start point and/or the end point satisfy imaging needs after the indicating device moves to the start point and/or the end point. If the start point and/or the end point satisfy the imaging needs, operation 640 may be executed to take the X-ray panoramic image. If the start point and/or the end point does not satisfy the imaging needs, positions of the start point and/or the end point may be modified. It should be understood that the positions of the start point and/or the end point may be manually modified by the doctor or the operator through adjusting the indicating device, or may be automatically modified by, for example, a position modification device.

It should be noted that the above description of the process 600 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

Figure 7:
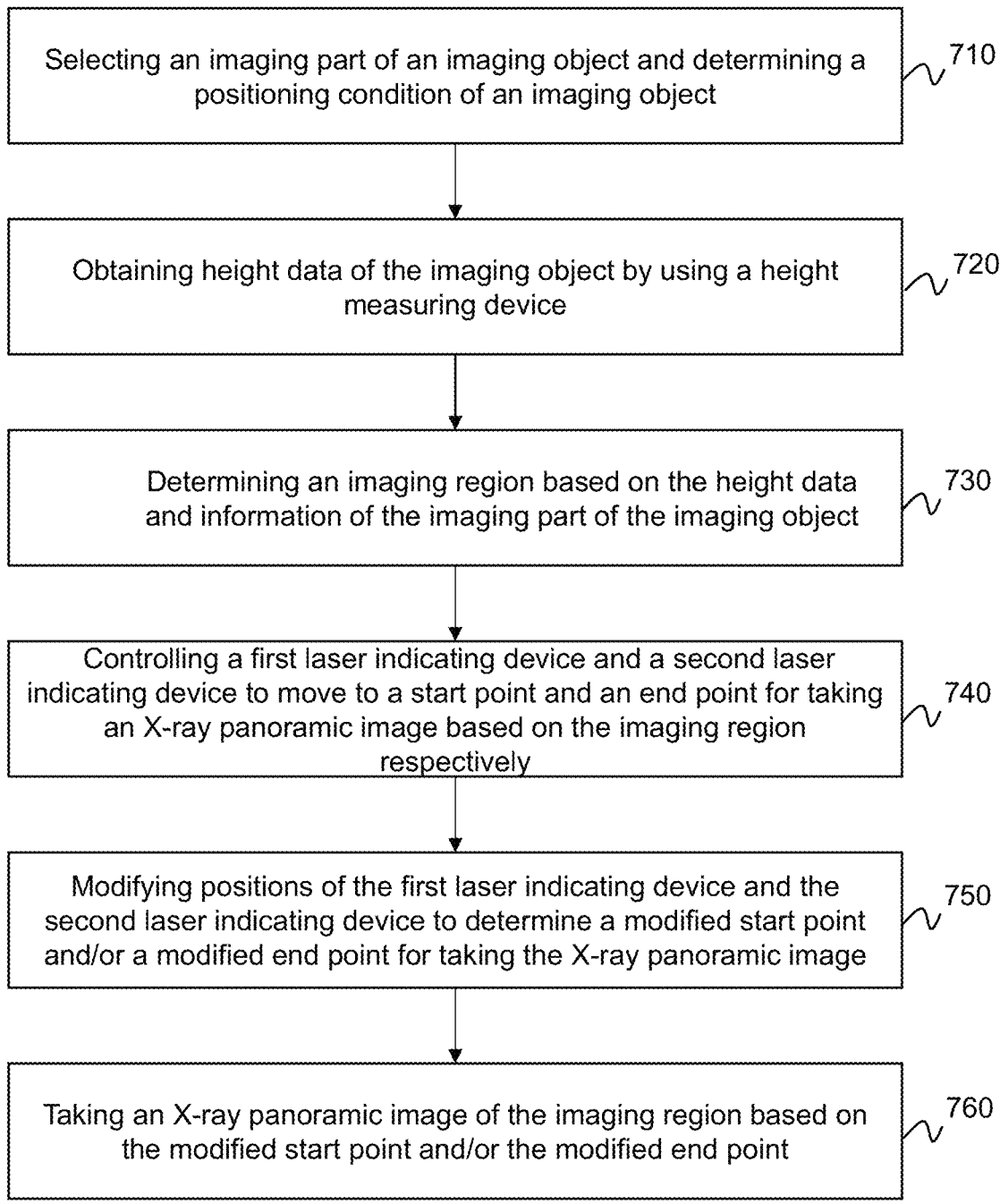
FIG. 7 is a flowchart illustrating an exemplary process for taking a medical image according to some embodiments of the present disclosure.

FIG. 7 is a flowchart illustrating an exemplary process for taking a medical image according to some embodiments of the present disclosure. In some embodiments, the indicating device may include a laser indicating device. The laser indicating device may include a first laser indicating device and a second laser indicating device. In some embodiments, at least part of process 700 may be performed by the processing device 140 (implemented in, for example, the computing device 200 shown in FIG. 2). For example, the process 700 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, or one or more modules illustrated in FIG. 12 or FIG. 13). The operations of the illustrated process presented below are intended to be illustrative. In some embodiments, the process 700 may be accomplished with one or more additional operations not described, and/or without one or more of the operations discussed. Additionally, the order in which the operations of the process 700 as illustrated in FIG. 7 and described below is not intended to be limiting.

In 710, an imaging part of an imaging object may be selected and a positioning condition of an imaging object may be determined.

Specifically, before an X-ray panoramic imaging is performed on an imaging part of an imaging object, the imaging part of the imaging object and a positioning condition of the imaging object should be determined. The imaging part of the imaging object and the positioning condition of the imaging object may be determined by the processing device 140 or may be manually determined by a doctor or an operator. The imaging part of the imaging object may include a body part with a relatively large range, such as a chest or a lower limb. The positioning condition of the imaging object may include a positive positioning condition, a lateral positioning condition, etc. After the positioning condition of the imaging object is determined, the imaging object should maintain posture and angle to prevent an inaccurate determination of the imaging region due to a change in standing height.

In 720, height data of the imaging object may be obtained by using a height measuring device (e.g., the height measuring device 430). The height data of the imaging object may be obtained by the processing device 140 (e.g., the obtaining module 1310 illustrated in FIG. 13) from the height measuring device.

Specifically, after the positioning condition of the imaging object is determined, a height measuring device installed on the support may measure a height of the imaging object to obtain the height data of the imaging object under the determined positioning condition of the imaging object. The obtained height data may be transmitted to the processor via, such as a wireless communication (e.g., the network 120).

In 730, an imaging region may be determined based on the height data and information of the imaging part of the imaging object. The imaging region may be determined by the processing device 140 (e.g., the determination module 1320 illustrated in FIG. 13).

Specifically, after receiving the height data and information of the imaging part of the imaging object, the processor may determine a region of the imaging part on a body of the imaging object based on the height data. The region of the imaging part on the body of the imaging object may be determined based on a physiological database associated with human body structure. Further, the processor may determine the imaging region for taking the X-ray panoramic image based on the region of the imaging part on the body of the imaging object. The imaging region may be the same as or different from the region of the imaging part on the body of the imaging object. For example, in order to ensure a certain amount of imaging margin, the imaging region may be larger than the region of the imaging part on the body of the imaging object.

In 740, the first laser indicating device and the second laser indicating device may be controlled to move to a start point and an end point for taking the X-ray panoramic image based on the imaging region respectively. The first laser indicating device and the second laser indicating device may be controlled by the processing device 140 (e.g., the determination module 1320 illustrated in FIG. 13).

Specifically, two laser indicating devices may be used to indicate the imaging region. The processor may control the first laser indicating device to move along the backboard of the support 410 to the start point and control the second laser indicating device to move along the backboard of the support 410 to the end point. Each laser indicating device may include an emitting unit and a receiving unit, wherein the receiving unit synchronously may move with the emitting unit and may be at a same height with the emitting unit and parallel to the baseboard of the support 410. In this situation, the region between a laser emitted by the emitting unit of the first laser indicating device and a laser emitted by the emitting unit of the second laser indicating device is the imaging region.

In 750, positions of the first laser indicating device and second laser indicating device may be modified to determine a modified start point and/or a modified end point for taking the X-ray panoramic image. The positions of the first laser indicating device and second laser indicating device may be modified by the processing device 140 (e.g., the determination module 1320 illustrated in FIG. 13).

Specifically, since a figure of the imaging object may be special (e.g., extremely high, extremely thin) or there may be an error in determining the imaging region, the start point and/or the end point may not satisfy actual imaging needs. After the first indicating device reaches the start point and the second indicating device reaches the end point, a doctor or an operator may determine whether the start point and/or the end point satisfy imaging needs. If the start point and/or the end point does not satisfy the imaging needs, the positions of the first laser indicating device and second laser indicating device may be modified. It should be understood that the positions of the first laser indicating device and second laser indicating device may be manually modified by the doctor or the operator, or may be automatically modified by, for example, a position modification device.

In 760, an X-ray panoramic image of the imaging region may be taken based on the modified start point and/or the modified end point. The X-ray panoramic image of the imaging region may be taken by the acquisition device 110 or by the processing device 140 (e.g., the imaging module 1330 illustrated in FIG. 13).

Specifically, after the modified start point and/or the modified end point are determined, an angle of the X-ray generator 113 may be adjusted, then the upper limit of the imaging range of the X-ray generator 113 reaches the modified start point. A bulb in the X-ray generator 113 may emit X-rays and the detector 112 may receive X-rays passing through the imaging object for taking a first image (also referred to as a "first intermediate image"). After the first image is taken, a target position for taking a second image may be determined by continuously adjusting the angle of the X-ray generator 113. Further, the detector 112 may synchronously move to the target position for taking a second image. A plurality of images may be taken by repeating the above X-ray imaging operation until the lower limit of the imaging range reaches the modified end point. The plurality of intermediate images obtained by the plurality of X-ray imaging operations may be stitched to obtain an X-ray panoramic image of the imaging part.

It should be noted that the above description of the process 700 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

Figure 8:
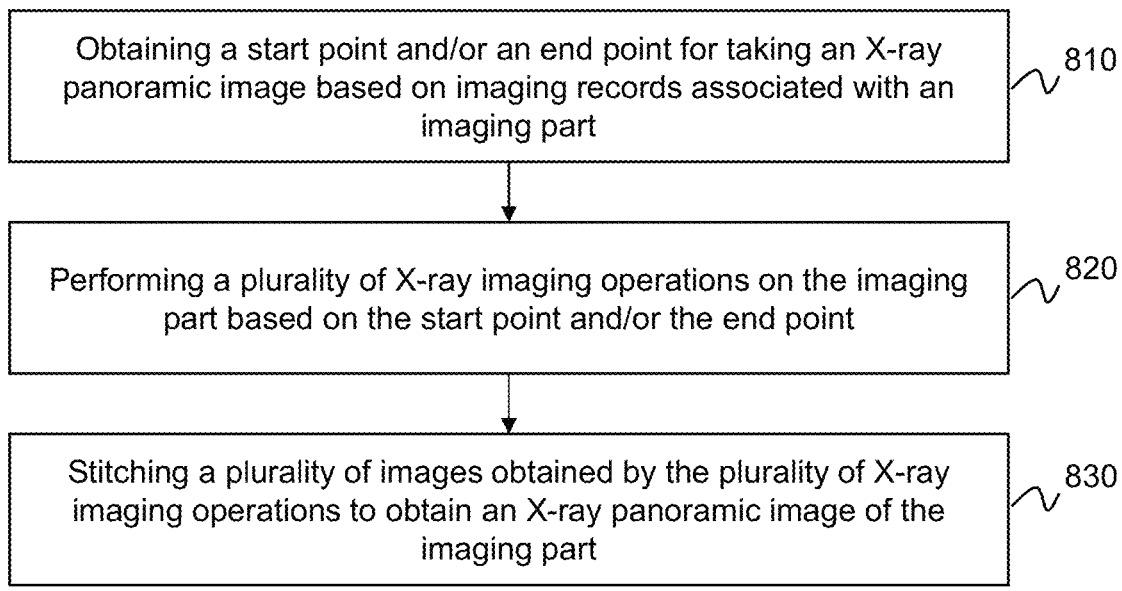
FIG. 8 is a flowchart illustrating an exemplary process for taking a medical image according to some embodiments of the present disclosure.

FIG. 8 is a flowchart illustrating an exemplary process for taking a medical image according to some embodiments of the present disclosure. As shown in FIG. 8, the medical imaging method may be applied to a medical imaging system for taking an X-ray panoramic image of an imaging part of an imaging object. In some embodiments, at least part of process 800 may be performed by the processing device 140 (implemented in, for example, the computing device 200 shown in FIG. 2). For example, the process 800 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, or one or more modules illustrated in FIG. 12 or FIG. 13). The operations of the illustrated process presented below are intended to be illustrative. In some embodiments, the process 800 may be accomplished with one or more additional operations not described, and/or without one or more of the operations discussed. Additionally, the order in which the operations of the process 800 as illustrated in FIG. 8 and described below is not intended to be limiting.

In 810, a start point and/or an end point for taking an X-ray panoramic image may be obtained based on imaging records (also referred to as "historical imaging records) associated with an imaging part (e.g., a chest, an upper abdomen, a lower abdomen, a spine, a lower limb) of an imaging object. The imaging records associated with the imaging part may be obtained by the processing device 140

Figure 13:
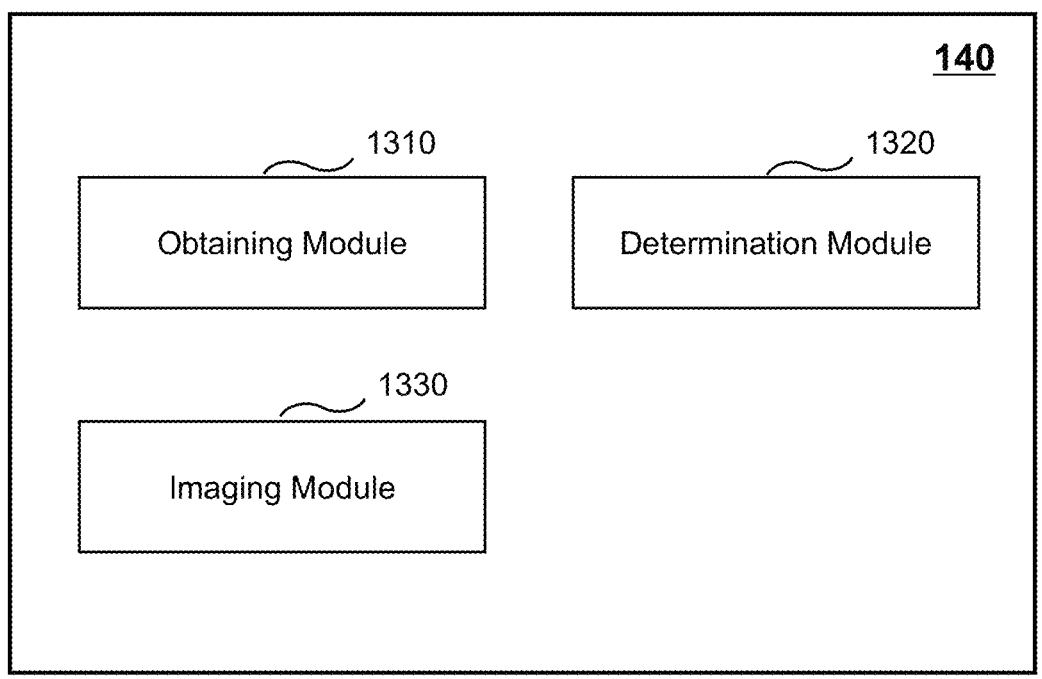
FIG. 13 is a block diagram illustrating an exemplary processing device according to some embodiments of the present disclosure.

(e.g., the obtaining module 1310 illustrated in FIG. 13). The start point and/or the end point for taking an X-ray panoramic image may be obtained by the processing device 140 (e.g., the determination module 1320 illustrated in FIG. 13).

In 820, a plurality of X-ray imaging operations may be performed on the imaging part based on the start point and/or the end point. The imaging records may include historical data of X-ray panoramic imaging operations performed on the imaging part of the imaging object. The plurality of X-ray imaging operations may be performed by the acquisition device 110 or by the processing device 140 (e.g., the imaging module 1330 illustrated in FIG. 13).

Specifically, before an X-ray panoramic image of an imaging part of an imaging object is taken, if a historical X-ray panoramic imaging was performed on the imaging part, imaging records storing a historical start point and/or a historical end point may be automatically obtained. After the start point and/or the end point are determined, a plurality of X-ray imaging operations may be performed from the start point to the end point and the X-ray panoramic image of the imaging part of the imaging object may be determined based on the plurality of X-ray images.

The imaging records may be obtained from local historical imaging data stored in the medical imaging system or a clinical history database via a network (e.g., the network 120). Thus, it is not required to re-determine a start point and/or an end point when taking an X-ray panoramic image of an imaging part of an imaging object. The medical imaging method also can be applied to a situation in which a plurality of X-ray panoramic images of the same imaging part under a plurality of positioning conditions need to be taken. After a first X-ray imaging operation is performed on the imaging part under a first positioning condition, a subsequent X-ray imaging operation may be performed on the same imaging part under a subsequent positioning condition based on the start point and/or the end point obtained in the first X-ray imaging operation.

During an imaging process, the imaging object may stand on the support 410 and the processor may determine whether the medical imaging system stores X-ray panoramic imaging records associated with the imaging part of the imaging object. If the medical imaging system stores the imaging records, the start point and/or the end point for taking the X-ray panoramic image may be automatically obtained based on the imaging records. An angle of the X-ray generator 113 may be adjusted based on the start point. A bulb in the X-ray generator 113 may emit X-rays and the detector 112 may receive X-rays passing through the imaging object for taking a first image (also referred to as a "first intermediate image"). After the first image is taken, a target position for taking a second image may be determined by continuously adjusting the angle of the X-ray generator 113. Further, the detector 112 may synchronously move along the support 410 to the target position for taking a second image. The X-ray panoramic imaging of the imaging part of the imaging object is completed until the entire imaging part is scanned.

According to above the medical imaging method, a start point and/or an end point for taking an X-ray panoramic image may be automatically obtained based on imaging records associated with an imaging part. When an X-ray panoramic imaging (which is not performed for the first time) is performed on the imaging part or X-ray panoramic imaging operations under different positioning conditions are performed on the imaging part, it is not required to re-determine a start point and/or an end point, which can effectively simplify the imaging process and decrease a time period during which the imaging object should maintain a positioning condition.

In 830, a plurality of images obtained by the plurality of X-ray imaging operations may be stitched to obtain an X-ray panoramic image of the imaging part. The plurality of images obtained by the plurality of X-ray imaging operations may be stitched by the processing device 140 (e.g., the imaging module 1330 illustrated in FIG. 13).

Specifically, a plurality of images may be captured by performing a plurality of imaging operations within the start and the end point. Further, a complete X-ray image (i.e., an X-ray panoramic image) of the imaging part from the start point to the end point may be determined by stitching the plurality of images.

It should be noted that the above description of the process 800 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

Figure 9:
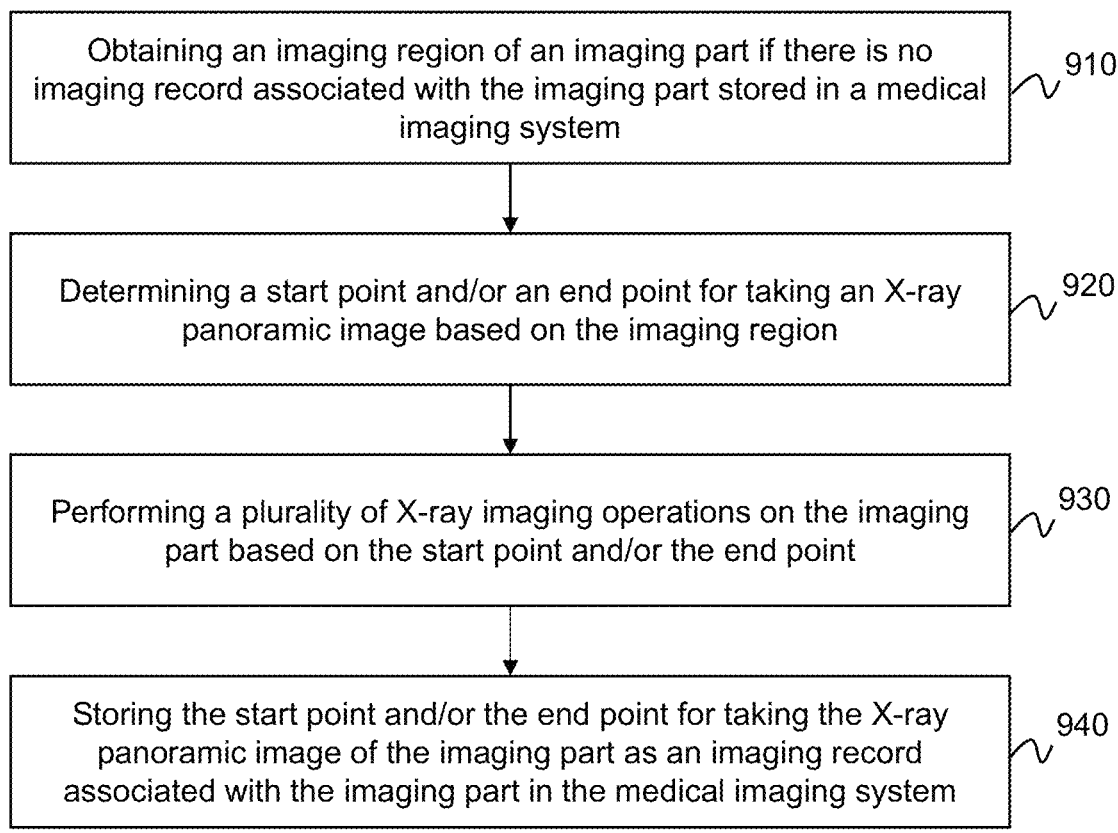
FIG. 9 is a flowchart illustrating an exemplary process for taking a medical image according to some embodiments of the present disclosure.

FIG. 9 is a flowchart illustrating an exemplary process for taking a medical image according to some embodiments of the present disclosure. In some embodiments, at least part of process 900 may be performed by the processing device 140 (implemented in, for example, the computing device 200 shown in FIG. 2). For example, the process 900 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, or one or more modules illustrated in FIG. 12 or FIG. 13). The operations of the illustrated process presented below are intended to be illustrative. In some embodiments, the process 900 may be accomplished with one or more additional operations not described, and/or without one or more of the operations discussed. Additionally, the order in which the operations of the process 900 as illustrated in FIG. 9 and described below is not intended to be limiting.

In 910, an imaging region of an imaging part may be obtained when no imaging record associated with the imaging part is stored in the medical imaging system. The imaging region of an imaging part may be obtained by the processing device 140 (e.g., the determination module 1320 illustrated in FIG. 13).

Specifically, if there is no imaging record associated with X-ray panoramic image(s) of the imaging part of the imaging object stored in the medical imaging system, for example, no X-ray imaging has been performed on the imaging part or historical imaging records were not stored, an imaging region of the imaging part of the imaging object may be obtained, which may be determined based on the imaging part and body features of the imaging object. The imaging region may be manually input into the medical imaging system by a doctor or an operator, or may be obtained by accessing medical history information of the imaging object. The imaging region may be the same as or different from a region of the imaging part on the body of the imaging object. For example, in order to ensure a certain amount of imaging margin, the imaging region may be larger than the region of the imaging part on the body of the imaging object.

In 920, a start point and/or an end point for taking an X-ray panoramic image may be determined based on the imaging region. The start point and/or an end point for taking an X-ray panoramic image may be determined by the processing device 140 (e.g., the determination module 1320 illustrated in FIG. 13).

Specifically, after a region of the imaging part of the imaging object on the body of the imaging object is determined, a start point and/or an end point for taking the X-ray panoramic image may be determined based on the region of the imaging part of the imaging object. The start point and/or end point may be determined by the processing device 140 based on the imaging region or manually input by a doctor or an operator. When determining the start point and/or the end point, not only the image region but also an imaging range of the X-ray generator 113 should be taken into consideration, thus a reasonable start point and/or a reasonable end point can be determined. Under the premise of ensuring the X-ray panoramic image of the imaging part is clear and complete, a number count of X-ray imaging operations can be reduced to facilitate subsequent stitching, an imaging process for taking an X-ray panoramic image can be shortened, and a time period during which the imaging object should maintain a positioning condition can be reduced.

In 930, a plurality of X-ray imaging operations may be performed on the imaging part based on the start point and/or the end point. The plurality of X-ray imaging operations may be performed by the acquisition device 110 or by the processing device 140 (e.g., the imaging module 1330 illustrated in FIG. 13).

Specifically, after the start point and/or the end point for taking the X-ray panoramic image are determined based on the imaging region of the imaging part, an angle of the X-ray generator 113 may be adjusted, then an edge of a coverage range of X-rays emitted by a bulb in the X-ray generator 113 reaches the start point. The detector 112 may receive X-rays passing through the imaging object for taking a first image (also referred to as a "first intermediate image"). After the first image is taken, a target position for taking a second image may be determined by continuously adjusting the angle of the X-ray generator 113. Further, the detector 112 may synchronously move along the support 410 to the target position for taking a second image. A plurality of images may be taken by repeating the above X-ray imaging operation until the edge of the coverage range of the X-rays reaches the end point. The plurality of intermediate images obtained by the plurality of X-ray imaging operations may be stitched to obtain an X-ray panoramic image of the imaging part.

In 940, the start point and/or the end point for taking the X-ray panoramic image of the imaging part may be stored as an imaging record associated with the imaging part in the medical imaging system.

Specifically, after the process for taking the X-ray panoramic image of the imaging part is completed, data including information of the imaging part of the imaging object and the start point and/or the end point for taking the X-ray panoramic image may be stored in the medical imaging system. Thus, when a next X-ray panoramic imaging needs to be performed, imaging records can be automatically accessed and a start point and/or an end point can be determined based on the imaging records, thereby omitting a positioning process for determining the start point and/or the end point.

In some embodiments, a simulated imaging may be performed based on the start point and/or the end point before a plurality of X-ray imaging operations are performed on the imaging part based on the start point and/or the end point.

The start point and/or the end point for taking the X-ray panoramic image may be modified if positions of the start point and/or the end point in the simulated imaging do not satisfy a preset condition.

Specifically, in some situations, for example, if a figure of the imaging object has changed compared with his/her figure at the time of the last X-ray imaging, the start point and/or the end point obtained based on imaging records may be deviated. Therefore, in order to avoid the deviation, before an X-ray imaging is performed, a simulated imaging may be performed based on the start point and/or the end point. A doctor or an operator can determine whether positions of the start point and/or the end point satisfy a preset condition based on a simulation result. If positions of the start point and/or the end point satisfy the preset condition, the X-ray imaging operation may continue. If positions of the start point and/or the end point do not satisfy the preset condition, the doctor or the operator may modify the start point and/or the end point to obtain a more accurate start point and/or a more accurate end point (also referred to as a modified start point and/or a modified end point) for taking the X-ray panoramic image.

Further, in order to facilitate the simulated imaging operation performed by the doctor or the operator, a simulation button may be set on a control interface of the medical imaging system. After the simulated imaging is started, the X-ray generator 113 may automatically adjust its height and/or angle (or may be adjusted by the processing device 140) based on the positions of the start point and/or the end point. The start point for taking the X-ray panoramic image may be indicated by an upper edge of a beam field of a beam limiter, and the end point for taking the X-ray panoramic image may be indicated by a lower edge of the beam field of the beam limiter. During the above process, it is not required to move the detector 112 or the chest radiograph box, and the doctor or the operator can perform an imaging confirmation or modify the positions of the start point and/or the end point based on the imaging region indicated by the beam field of the beam limiter. It should be understood that any other device such as a laser indicating device may also be used to indicate the positions of the start point and/or the end point for the simulated imaging for taking the X-ray panoramic image.

It should be noted that the above description of the process 900 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

Figure 10:
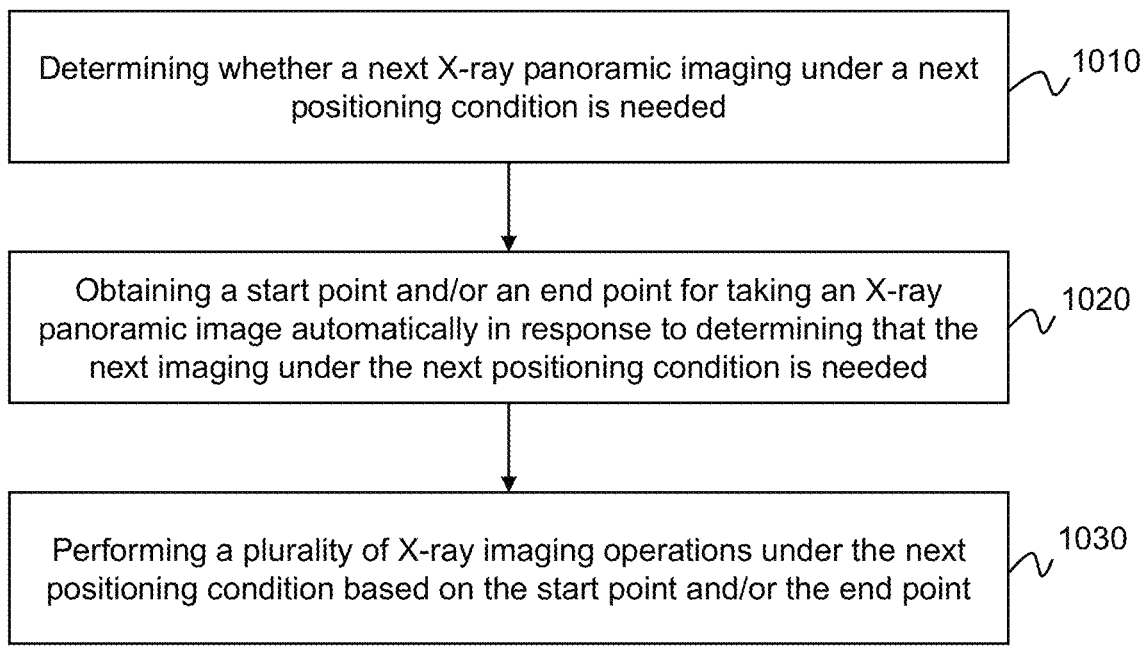
FIG. 10 is a flowchart illustrating an exemplary process for taking a medical image according to some embodiments of the present disclosure.

FIG. 10 is a flowchart illustrating an exemplary process for taking a medical image according to some embodiments of the present disclosure. In some embodiments, at least part of process 1000 may be performed by the processing device 140 (implemented in, for example, the computing device 200 shown in FIG. 2). For example, the process 1000 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, or one or more modules illustrated in FIG. 12 or FIG. 13). The operations of the illustrated process presented below are intended to be illustrative. In some embodiments, the process 1000 may be accomplished with one or more additional operations not described, and/or without one or more of the operations discussed. Additionally, the order in which the operations of the process 1000 as illustrated in FIG. 10 and described below is not intended to be limiting.

In 1010, whether a next X-ray panoramic imaging under a next positioning condition is needed may be determined. The determination may be performed by the processing device 140 (e.g., the determination module 1320 or the imaging module 1330 illustrated in FIG. 13).

In 1020, if it is determined that the next imaging under the next positioning condition is needed, a start point and/or an end point for taking an X-ray panoramic image may be automatically obtained. The start point and/or the end point for taking the X-ray panoramic image may be automatically obtained by the processing device 140 (e.g., the determination module 1320 illustrated in FIG. 13).

In 1030, a plurality of X-ray imaging operations under the next positioning condition may be performed based on the start point and/or the end point. The plurality of X-ray imaging operations may be performed by the acquisition device 110 or by the processing device 140 (e.g., the imaging module 1330 illustrated in FIG. 13).

Specifically, after a first X-ray imaging operation is performed on an imaging part of an imaging object, whether a next X-ray panoramic imaging under a next positioning condition is needed may be determined. The determination may be manually performed by a doctor or an operator, or may be automatically performed by the processing device 140 based on medical records of the imaging object. If the next imaging under the next positioning condition is needed, the start point and/or the end point in the first X-ray imaging operation may be automatically obtained. Further, a plurality of X-ray imaging operations under a subsequent positioning condition may be performed based on the start point and/or end point obtained in the first X-ray imaging operation. When an X-ray panoramic imaging (which is not performed for the first time) is performed on the imaging part or X-ray panoramic imaging operations under different positioning conditions are performed on the imaging part, it is not required to re-determine a start point and/or an end point, which can effectively simplify the imaging process and decrease a time period during which the imaging object should maintain a positioning condition.

It should be noted that the above description of the process 1000 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

Figure 11:
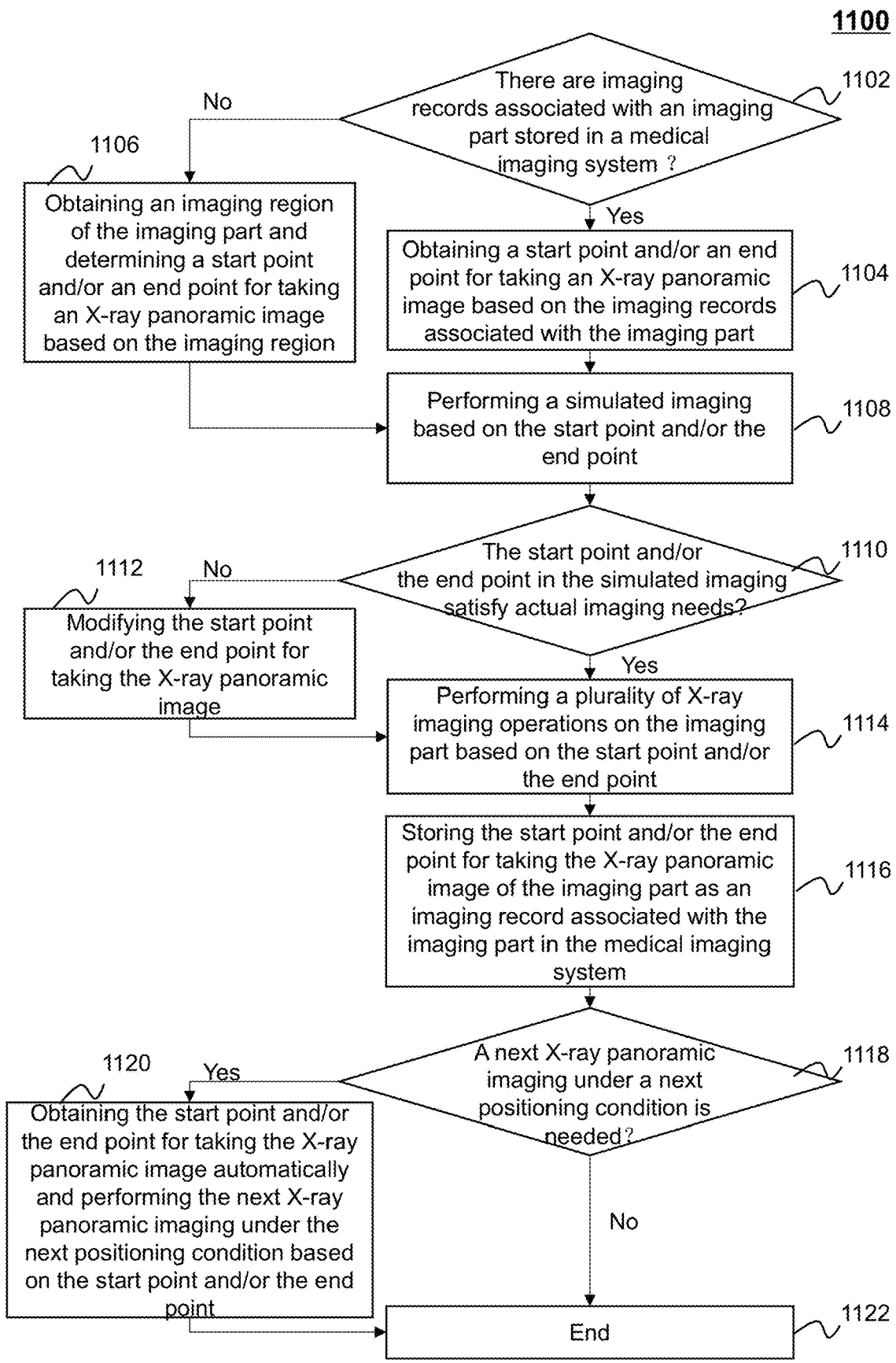
FIG. 11 is a flowchart illustrating an exemplary process for taking a medical image according to some embodiments of the present disclosure.

FIG. 11 is a flowchart illustrating an exemplary process for taking a medical image according to some embodiments of the present disclosure. In some embodiments, at least part of process 1100 may be performed by the processing device 140 (implemented in, for example, the computing device 200 shown in FIG. 2). For example, the process 1100 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, or one or more modules illustrated in FIG. 12 or FIG. 13). The operations of the illustrated process presented below are intended to be illustrative. In some embodiments, the process 1100 may be accomplished with one or more additional operations not described, and/or without one or more of the operations discussed. Additionally, the order in which the operations of the process 1100 as illustrated in FIG. 11 and described below is not intended to be limiting.

In 1102, whether there are imaging records associated with an imaging part stored in a medical imaging system may be determined. The determination may be performed by the processing device 140 (e.g., the determination module 1320 or the imaging module 1330 illustrated in FIG. 13).

Specifically, when an X-ray panoramic imaging is performed on an imaging object, an imaging part of the imaging object should be determined. The imaging part of the imaging object may include a body part such as a chest, an upper abdomen, a lower abdomen, a spine, a lower limb, etc. After the imaging part of the imaging object is determined, whether there are imaging records associated with the imaging part stored in the medical imaging system may be determined. If it is determined that there are imaging records associated with the imaging part stored in the medical imaging system, the imaging records associated with the imaging part may be obtained from the medical imaging system and operation 1104 may be executed. If it is determined that there is no imaging record associated with the imaging part stored in the medical imaging system, operation 1106 may be executed.

In 1104, a start point and/or an end point for taking an X-ray panoramic image may be obtained based on the imaging records associated with the imaging part. The start point and/or the end point for taking the X-ray panoramic image may be obtained by the processing device 140 (e.g., the determination module 1320 illustrated in FIG. 13).

Specifically, after the imaging records associated with the imaging part are obtained from the medical imaging system, which may store information (e.g., information of the imaging part of the imaging object) associated with the imaging object and historical X-ray panoramic imaging data, a start point and/or an end point may be obtained from the imaging records and operation 1108 may be executed.

In 1106, an imaging region of the imaging part may be obtained and a start point and/or an end point for taking an X-ray panoramic image may be determined based on the imaging region. The imaging region of the imaging part and/or the start point and/or the end point for taking the X-ray panoramic image may be determined by the processing device 140 (e.g., the determination module 1320 illustrated in FIG. 13).

Specifically, if there is no imaging record associated with the imaging part stored in the medical imaging system, it may indicate that it may be the first time to take an X-ray panoramic image of the imaging part of the imaging object. Then an imaging region of the imaging part of the imaging object may be determined, which may be manually input into the medical imaging system by a doctor or an operator or may be determined based on height data of the imaging object (see, e.g., FIGS. 4-7 and the descriptions thereof). According to the imaging region, position information of the imaging region on a body of the imaging object can be determined, then position information of a start point and/or an end point for taking an X-ray panoramic image can be determined, and operation 1108 may be further executed.

In 1108, a simulated imaging may be performed based on the start point and/or the end point. The simulated imaging may be performed by the processing device 140 (e.g., the imaging module 1330 illustrated in FIG. 13).

Specifically, after the start point and/or the end point for taking the X-ray panoramic image are obtained in operation 1104 or in operation 1106, in order to ensure the accuracy of the imaging region and prevent that the imaging region deviates from actual imaging needs due to changes in a body size or a special body size of the imaging object, a simulated imaging may be performed through a beam field of a beam limiter which is used to indicate positions of the start point and/or the end point and the positions of the start point and/or the end point may be presented to a doctor or an operator to be confirmed.

In 1110, whether the start point and/or the end point in the simulated imaging satisfy actual imaging needs may be determined. The determination may be performed by the processing device 140 (e.g., the determination module 1320 illustrated in FIG. 13).

Specifically, in operation 1108, after the positions of the start point and/or end point are presented to the doctor or the operator to be confirmed, if the doctor or the operator determines that the positions of the start point and/or the end point indicated in the simulated imaging do not satisfy the actual imaging needs, operation 1112 may be executed. If the doctor or the operator determines that the positions of the start point and/or the end point indicated in the simulated imaging satisfy the actual imaging needs, operation 1114 may be executed.

In 1112, the start point and/or the end point for taking the X-ray panoramic image may be modified. The start point and/or the end point may be modified by the processing device 140 (e.g., the determination module 1320 illustrated in FIG. 13).

Specifically, if the positions of the start point and/or the end point indicated in the simulated imaging do not satisfy the actual imaging needs, the positions of the start point and/or the end point may be modified. The doctor or the operator may manually modify a beam field range of the beam limiter to determine a modified start point and/or a modified end point. Also, the doctor or the operator may remotely control a modification device to modify the positions of the start point and/or the end point. Further, the positions of the start point and/or the end point may also be automatically modified by the processing device 140 to satisfy the actual imaging needs. After the positions of the start point and/or the end point are modified, operation 1114 may be executed.

In 1114, a plurality of X-ray imaging operations may be performed on the imaging part based on the start point and/or the end point. The plurality of X-ray imaging operations may be performed by the acquisition device 110 or by the processing device 140 (e.g., the imaging module 1330 illustrated in FIG. 13).

Specifically, if the positions of the start point and/or the end point satisfy the actual imaging needs, an X-ray imaging operation may be performed on the imaging part of the imaging object based on the start point and/or the end point by controlling the imaging device 110. The plurality of X-ray imaging operations may be performed on the imaging part from the start point to the end point to obtain a plurality of images of the imaging part. Further, the plurality of obtained images may be stitched to obtain an X-ray panoramic image of the imaging part. After the plurality of X-ray imaging operations are completed, operation 1116 may be executed.

In 1116, the start point and/or the end point for taking the X-ray panoramic image of the imaging part may be stored as an imaging record associated with the imaging part in the medical imaging system.

Specifically, after the X-ray panoramic imaging performed on the imaging part is completed, data including information of the imaging object, positioning information of the X-ray panoramic imaging, and the positon information of the start point and/or the end point may be stored as imaging records in the medical imaging system. Thus, when a next X-ray panoramic imaging is performed on the imaging part of the imaging object, the start point and/or the end point for taking the X-ray panoramic image can be automatically obtained from the imaging records. Since in actual X-ray panoramic imaging, it is usually needed to perform a plurality of X-ray panoramic imaging operations on the imaging part under different positioning conditions, the imaging record of the current X-ray panoramic imaging is stored and operation 1118 may be executed.

In 1118, whether a next X-ray panoramic imaging under a next positioning condition is needed may be determined. The determination may be performed by the processing device 140 (e.g., the determination module 1320 illustrated in FIG. 13).

Specifically, after an X-ray imaging performed on the imaging part under a positioning condition is completed, whether a next X-ray panoramic imaging on the imaging part under a next positioning is needed may be determined. For example, after images of the imaging part of the imaging object under a positive positioning condition are stitched, whether an X-ray panoramic imaging under a lateral positioning condition is needed for the imaging part of the imaging object may be determined. If the X-ray panoramic imaging under the lateral positioning condition is needed for the imaging part of the imaging object, operation 1120 may be executed. If an X-ray panoramic imaging under the lateral positioning condition is not needed for the imaging part of the imaging object, operation 1122 may be executed.

In 1120, the start point and/or the end point for taking the X-ray panoramic image may be automatically obtained and a next X-ray panoramic imaging under a next positioning condition may be performed based on the start point and/or the end point. The start point and/or the end point for taking the X-ray panoramic image may be automatically obtained by the processing device 140 (e.g., the determination module 1320 illustrated in FIG. 13) and the next X-ray panoramic imaging under the next positioning condition may be performed by the processing device 140 (e.g., the imaging module 1330 illustrated in FIG. 13).

Specifically, if it is determined that a next X-ray panoramic imaging under a next positioning condition is needed, the next X-ray panoramic imaging (e.g., a second X-ray panoramic imaging) may be performed under the next positioning condition (e.g., a second positioning condition) after a first X-ray panoramic imaging under a first positioning condition is completed. For the second X-ray panoramic imaging under the second positioning condition, the start point and/or the end point for taking the X-ray panoramic image under the first positioning condition may be automatically obtained and the acquisition device 110 may be controlled to perform the second X-ray panoramic imaging on the imaging part under the second positioning condition after it is determined that the positioning condition of the imaging object is correct. Further, after the second X-ray panoramic imaging is completed, whether a next X-ray panoramic imaging under a next positioning condition is needed may be determined. If it is determined that a next X-ray panoramic imaging under a next positioning condition is needed, the next X-ray panoramic imaging (e.g., a third X-ray panoramic imaging) under the next positioning condition (e.g., a third positioning condition) may be performed based on the start point and/or the end point for taking the X-ray panoramic image under the first positioning condition until X-ray panoramic imaging operations under all positioning conditions are completed and operation 1122 may be executed.

In 1122, the X-ray panoramic imaging may be ended. The X-ray panoramic imaging may be ended by the processing device 140 (e.g., the imaging module 1330 illustrated in FIG. 13).

Specifically, if only one X-ray panoramic imaging under a single positioning condition is needed for the imaging part or X-ray panoramic imaging operations under all positioning condition have been completed, a plurality of obtained images (also referred to as "intermediate images") may be stitched to determine a complete X-ray panoramic image of the imaging part. Then the process for taking the X-ray panoramic image may be ended.

It should be noted that the above description of the process 11000 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

Figure 12:
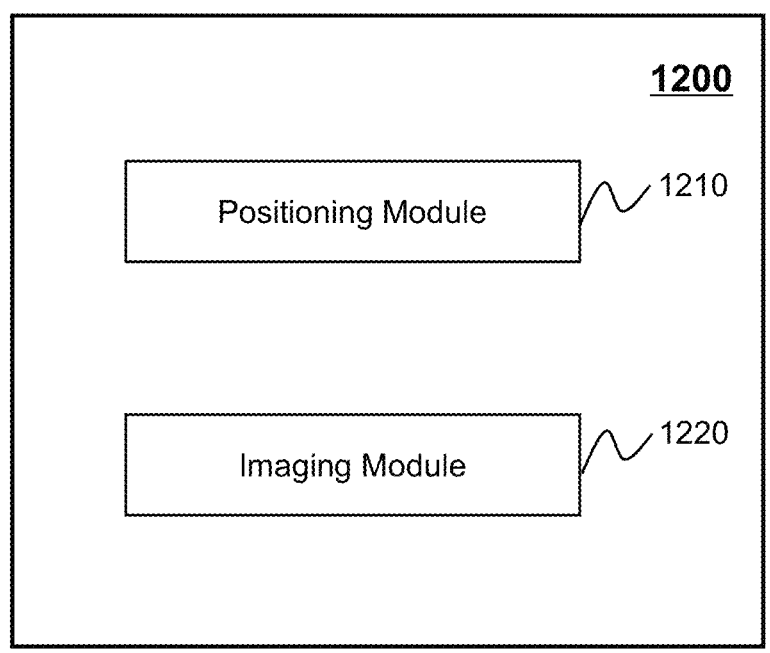
FIG. 12 is a block diagram illustrating an exemplary medical imaging device according to some embodiments of the present disclosure.

FIG. 12 is a block diagram illustrating an exemplary medical imaging device according to some embodiments of the present disclosure. As illustrated, the medical imaging device 1200 may include a positioning module 1210 and an imaging module 1220. In some embodiments, the medical imaging device 1200 may be integrated into the processing device 140.

The positioning module 1210 may be configured to obtain a start point and/or an end point for taking an X-ray panoramic image based on imaging records associated with an imaging part (e.g., a chest, an upper abdomen, a lower abdomen, a spine, a lower limb) of an imaging object. The imaging records may include historical data of X-ray panoramic imaging operations performed on the imaging part of the object. The imaging module 1220 may be configured to perform an X-ray panoramic imaging operation on the imaging part based on the start point and/or the end point.

Specifically, the positioning module 1210 may determine whether a historical X-ray panoramic imaging was performed on the imaging part. If the historical X-ray panoramic imaging was performed on the imaging part, the positioning module 1210 may obtain a historical imaging region of the imaging part based on an imaging record storing a historical start point and/or a historical end point. Further, the positioning module 1210 may determine the start point and/or end point based on the imaging record and transmit the start point and/or the end point to the imaging module 1220. The imaging module 1220 may control the medical imaging device 1200 to perform an X-ray panoramic imaging operation on the imaging part of the imaging object from the start point to the end point.

According to the above medical imaging device, a start point and/or an end point for taking an X-ray panoramic image may be automatically obtained based on imaging records associated with an imaging part. When an X-ray panoramic imaging (which is not performed for the first time) is performed on the imaging part or X-ray panoramic imaging operations under different positioning conditions are performed on the imaging part, it is not required to re-determine a start point and/or an end point, which can effectively simplify the imaging process and decrease a time period during which the imaging object should maintain a positioning condition.

The modules in the medical imaging device 1200 may be connected to or communicated with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof.

In some embodiments, the present disclosure may also provide a medical imaging system including a storage, a processor, and a computer program stored in the storage and executed by the processor. When the processor executes the computer program, a process (e.g., process 500, process 600, process 700, process 800, process 900, process 1000, process 1100) described elsewhere in the present disclosure may be implemented.

In some embodiments, the present disclosure may also provide a computer readable storage medium storing a computer program. When the computer program is executed by a processor, a process (e.g., process 500, process 600, process 700, process 800, process 900, process 1000, process 1100) described elsewhere in the present disclosure may be implemented.

FIG. 13 is a block diagram illustrating an exemplary processing device according to some embodiments of the present disclosure. The processing device 140 may include an obtaining module 1310, a determination module 1320, and an imaging module 1330.

The obtaining module 1310 may be configured to obtain reference data associated with an object (also referred to as an "imaging object") (e.g., a patient). In some embodiments, the reference data may include height data of the object, historical data (e.g., historical imaging records) associated with the object, or the like, or a combination thereof. In some embodiments, as described in connection with FIG. 4 and FIG. 6, the obtaining module 1310 may obtain the height data of the object from a height measuring device (e.g., the height measuring device 430). In some embodiments, as described in connection with FIG. 8, the obtaining module 1310 may obtain the historical data associated with the object from a storage device (e.g., the storage device 150, the storage 220, the storage 390) disclosed elsewhere in the present disclosure.

The determination module 1320 may be configured to determine at least one of a start point or an end point of an imaging region associated with the object based on the reference data. In some embodiments, the imaging region may be associated with a predetermined body part (also referred to as an "imaging part") (e.g., a chest, an upper abdomen, a lower abdomen) of the object. The imaging region may be the same as or different from a region of the predetermined body part on a body of the object. In some embodiments, the determination module 1320 may determine at least one of the start point or the end point of the imaging region based on the height data and the predetermined body part of the object. In some embodiments, the determination module 1320 may determine the at least one of the start point or the end point of the imaging region based on the historical data associated with an object.

The imaging module 1330 may be configured to cause an imaging device (e.g., the acquisition device 110) to take an X-ray image (e.g., an X-ray panoramic image) of the imaging region based on at least one of the start point or the end point. In some embodiments, as described elsewhere in the present disclosure, the imaging module 1330 may cause the imaging device 110 to capture a plurality of intermediate images by performing a plurality of imaging operations within the start point and the end point and determine the X-ray image by stitching the plurality of intermediate images. In some embodiments, during the imaging process, the imaging module 1330 may transmit a control signal associated with at least one of the start point or the end point to an indicating device (e.g., the indicating device 420 illustrated in FIG. 4).

In some embodiments, before causing the imaging device to take the X-ray image of the imaging region, the determination module 1320 may determine whether the start point or the end point needs to be modified. In response to determining that the start point or the end point needs to be modified, the determination module1 320 may determine a modified start point or a modified end point.

In some embodiments, after the imaging process is completed, the determination module 1320 or the imaging module 1330 may determine whether a next imaging under a next positioning condition is needed. In response to determining that the next imaging under the next positioning condition is needed, the determination module 1320 may automatically obtain the start point and the end point under the first positioning condition and the imaging module 1330 may perform the next imaging under the next positioning condition based on the start point and end point.

The modules in the processing device 140 may be connected to or communicated with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof. Two or more of the modules may be combined into a single module, and any one of the modules may be divided into two or more units. For example, the processing device 140 may further include an I/O unit for facilitating interactions between the X-ray imaging system 100 and a user. As another example, the processing device 140 may include a storage module (not shown) used to store information and/or data (e.g., the start point, the end point, the imaging region) associated with the object.

Figure 14:
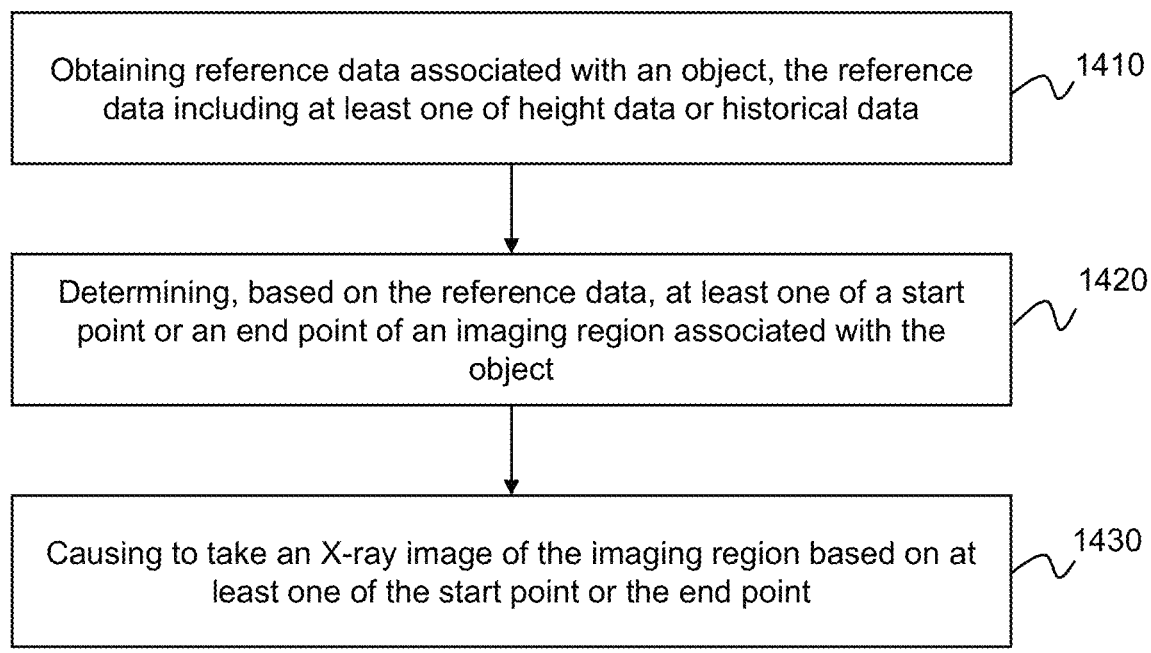
FIG. 14 is a flowchart illustrating an exemplary process for taking an X-ray image according to some embodiments of the present disclosure.

FIG. 14 is a flowchart illustrating an exemplary process for taking X-ray images according to some embodiments of the present disclosure. In some embodiments, at least part of process 1400 may be performed by the processing device 140 (implemented in, for example, the computing device 200 shown in FIG. 2). For example, the process 1400 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, or one or more modules illustrated in FIG. 12 or FIG. 13). The operations of the illustrated process presented below are intended to be illustrative. In some embodiments, the process 1400 may be accomplished with one or more additional operations not described, and/or without one or more of the operations discussed. Additionally, the order in which the operations of the process 1400 as illustrated in FIG. 14 and described below is not intended to be limiting.

In 1410, the processing device 140 (e.g., the obtaining module 1310) may obtain reference data associated with an object (also referred to as an "imaging object") (e.g., a patient). In some embodiments, the reference data may include height data of the object, historical data (e.g., historical imaging records) associated with the object, or the like, or a combination thereof.

In some embodiments, as described in connection with FIG. 4 and FIG. 6, the processing device 140 may obtain the height data of the object from a height measuring device (e.g., the height measuring device 430). The height measuring device may be an infrared measuring device, an ultrasonic measuring device, or any other measuring device which can be used to measure a height of an object for an ordinary person in the art. In some embodiments, as described in connection with FIG. 8, the processing device 140 may obtain the historical data associated with the object from a storage device (e.g., the storage device 150, the storage 220, the storage 390) disclosed elsewhere in the present disclosure.

In 1420, the processing device 140 (e.g., the determination module 1320) may determine at least one of a start point or an end point of an imaging region associated with the object based on the reference data. As used herein, the imaging region refers to a region within which X-rays may be emitted and an imaging operation may be performed based on the emitted X-rays.

In some embodiments, the imaging region may be associated with a predetermined body part (also referred to as an "imaging part") (e.g., a chest, an upper abdomen, a lower abdomen, a spine, a lower limb) of the object. The imaging region may be the same as or different from a region of the predetermined body part on a body of the object. For example, in order to ensure a certain amount of imaging margin, the imaging region may be larger than the region of the predetermined body part on the body of the object.

In some embodiments, the processing device 140 may determine at least one of the start point or the end point of the imaging region based on the height data and the predetermined body part of the object. For example, as described in connection with process 600, the processing device 140 may determine the region of the predetermined body part on the body of the object based on the height of the object and a relationship between "height" and "body part," determine the imaging region based on the region of the predetermined part, and determine the start point or the end point of the imaging region. As used herein, the relationship between "height" and "body part" may be a relationship indicating a range of any body part in a height range of an object.

In some embodiments, the relationship between "height" and "body part" may be determined based on statistical data or big data. For example, the processing device 140 may define a plurality of features (e.g., "age," "gender," "native place," "medical history") and obtain height data associated with the plurality of features. Further, the processing device 140 may determine a plurality of candidate relationships between "height" and "body part" associated with the plurality of features based on the height data. When determining the region of the body part on the body of the object, the processing device 140 may determine object information (e.g., age, gender, native place, medical history) of the object, identify a target relationship between "height" and "body part" from the plurality of candidate relationships based on the object information, and determine the region of the predetermined body part on the body of the object based on the height of the object and the target relationship between "height" and "body part."

In some embodiments, the processing device 140 may determine at least one of the start point or the end point of the imaging region based on the historical data associated with the object. For example, as described in connection with process 800, it is assumed that a historical imaging was performed on the same body part, the processing device 140 may automatically obtain historical data (e.g., historical imaging records) associated with the object storing a historical start point and/or a historical end point and determine the at least one of the start point or the end point of the imaging region based on the historical data.

In 1430, the processing device 140 (e.g., the imaging module 1330) may cause an imaging device (e.g., the acquisition device 110) to take an X-ray image (e.g., an X-ray panoramic image) of the imaging region based on at least one of the start point or the end point, or the processing device 140 (e.g., the imaging module 1330) may take the X-ray image of the imaging region based on at least one of the start point or the end point. As used herein, the term "take" refers to an operation including capturing images and/or processing images (e.g., stitching images).

In some embodiments, as described elsewhere in the present disclosure, since a projection range of X-rays emitted (i.e., an imaging range of the X-ray generator) by the X-ray generator 113 is limited, in order to determine an X-ray panoramic image, it is required to perform a plurality of imaging operations (also referred to as "intermediate imaging operation") within the start point and the end point. The processing device 140 may cause the acquisition device 110 to capture a plurality of intermediate images by performing a plurality of imaging operations within the start point and the end point and determine the X-ray image by stitching the plurality of intermediate images.

In some embodiments, during the imaging process, the processing device 140 may transmit a control signal associated with at least one of the start point or the end point to an indicating device (e.g., the indicating device 420 illustrated in FIG. 4). In some embodiments, the indicating device may be movably installed on a support (e.g., the support 410 in FIG. 4) for carrying the object and may move on the backboard of the support to present at least one of the start point or the end point while taking the X-ray image. In some embodiments, the indicating device may include a laser indicating device, a mechanical device (e.g., a ruler), or the like, or a combination thereof. The laser indicating device may include a first laser indicating device configured to indicate the start point and a second laser indicating device configured to indicate the end point. Each laser indicating device may include an emitting unit and a receiving unit, wherein the receiving unit may synchronously move with the emitting unit and may be at a same height with the emitting unit. More descriptions of the indicating device may be found elsewhere in the present disclosure (e.g., FIG. 5 and the description thereof).

In some embodiments, before causing the imaging device to take the X-ray image of the imaging region, the processing device 140 may determine whether the start point or the end point needs to be modified.

For example, the processing device 140 may determine whether the object corresponds to a predetermined category (e.g., the disabled). In response to determining that the object corresponds to a predetermined category, the processing device 140 may determine that the start point or the end point needs to be modified.

As another example, the processing device 140 may perform (or cause the imaging device to perform) a simulated imaging based on the start point and the end point and determine whether the start point or the end point satisfies a preset condition (e.g., actual imaging needs, field of view of the imaging device) based on a simulation result. In response to determining that the start point or the end point do not satisfy the preset condition, the processing device 140 may determine that the start point or the end point needs to be modified.

As a further example, the processing device 140 may send the start point and/or the end point to a doctor or an operator and determine that the start point or the end point needs to be modified based on a modification advice from the doctor or the operator.

In response to determining that the start point or the end point needs to be modified, the processing device 140 (e.g., a position modification device) may determine a modified start point or a modified end point. The processing device 140 may also modify positions of the first laser indicating device or second laser indicating device to present the modified start point or the modified end point. In some embodiments, the modified start point or the modified end point may be manually modified by the doctor or the operator.

In some embodiments, after the imaging process is completed, the processing device 140 may determine whether a next imaging under a next positioning condition is needed. As described elsewhere in the present disclosure, after a first imaging under a first positioning condition is completed, the processing device 140 may further determine whether a next imaging (e.g., a second imaging) under a next positioning condition (e.g., a second positioning condition) is needed. In response to determining that the next imaging under the next positioning condition is needed, the processing device 140 may automatically obtain the start point and/or the end point under the first positioning condition and perform the second imaging under the second positioning condition based on the start point and/or end point. After the second imaging is completed, the processing device 140 may further determine whether a next imaging (e.g., a third imaging) under a next positioning (e.g., a third positioning condition) is needed. In response to determining that the next imaging under the next positioning condition is needed, the processing device 140 may perform the third imaging under the third positioning condition based on the start point and the end point under the first positioning condition until imaging operations under all positioning conditions are completed.

It should be noted that the above description of the process 1400 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, one or more other optional operations (e.g., a storing operation) may be added elsewhere in the process 1400. In the storing operation, information and/or data (e.g., the start point, the end point, the imaging region) associated with the object may be stored in a storage device (e.g., the storage device 150, the storage 220, the storage 390) disclosed elsewhere in the present disclosure. As another example, the start point and/or the end point may be stored as an imaging record associated with the object in a storage device, which can be provided as reference information for subsequent imaging.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this disclosure are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction performing system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. A method for taking X-ray images, implemented on a computing device including a processor and a storage, comprising:
    obtaining reference data associated with an object, the reference data comprising at least one of height data or historical data;
    determining, based on the reference data, at least one of a start point or an end point of an imaging region associated with the object;
    determining whether the start point or the end point needs to be modified;
    in response to determining that the start point or the end point needs to be modified, performing a simulated imaging based on the start point and the end point;
    determining, based on a simulation result, whether the start point or the end point satisfies a preset condition;
    determining a modified start point or a modified end point in response to determining that the start point or the end point does not satisfy the preset condition; and
    causing an acquisition device to take an X-ray image of the imaging region based on the start point and the end point, the start point and the modified end point, the modified start point and the end point, or the modified start point and the modified end point.

2. The method of claim 1, further comprising:
    obtaining the height data using a height measuring device.

3. The method of claim 1, further comprising:
    transmitting a control signal associated with at least one of the start point or the end point to an indicating device, wherein the indicating device is to present at least one of the start point or the end point while taking the X-ray image.

4. The method of claim 1, wherein the determining, based on the reference data, at least one of the start point or the end point of the imaging region associated with the object comprises:
    determining at least one of the start point or the end point of the imaging region based on the height data and a predetermined body part of the object.

5. The method of claim 1, wherein the causing the acquisition device to take the X-ray image of the imaging region based the start point and the end point, the start point and the modified end point, the modified start point and the end point, or the modified start point and the modified end point comprises:
    capturing a plurality of intermediate images by performing a plurality of imaging operations within the start point and the end point, the start point and the modified end point, the modified start point and the end point, or the modified start point and the modified end point; and
    determining the X-ray image by stitching the plurality of intermediate images.

6. The method of claim 1, further comprising:
    determining whether a next imaging under a next positioning condition is needed;
    obtaining the start point and the end point automatically in response to determining that the next imaging under the next positioning condition is needed; and
    performing the next imaging under the next positioning condition based on the start point and the end point.

7. The method of claim 1, wherein the X-ray image of the imaging region is a panoramic image.

8. The method of claim 3, wherein the indicating device is movably installed on a support for carrying the imaging object.

9. The method of claim 3, wherein the indicating device comprises a laser indicating device.

10. The method of claim 9, wherein the laser indicating device comprises an emitting unit and a receiving unit, the receiving unit synchronously moving with the emitting unit and being at a same height with the emitting unit.

11. A system for X-ray imaging, comprising:
    an acquisition device including an X-ray source and an X-ray detector;
    a storage medium to store a set of instructions; and
    a processor, communicatively coupled to the storage medium, to execute the set of instructions to:
        obtain reference data associated with an object, the reference data comprising at least one of height data or historical data;
        determine, based on the reference data, at least one of a start point or an end point of an imaging region associated with the object;
        determine whether the start point or the end point needs to be modified;
        in response to determining that the start point or the end point needs to be modified, perform a simulated imaging based on the start point and the end point;
        determine, based on a simulation result, whether the start point or the end point satisfies a preset condition;
        determine a modified start point or a modified end point in response to determining that the start point or the end point does not satisfy the preset condition; and
        cause the acquisition device to take an X-ray image of the imaging region based on the start point and the end point, the start point and the modified end point, the modified start point and the end point, or the modified start point and the modified end point.

12. The system of claim 11, further comprising a height measuring device, wherein the processor is further to:
    obtain the height data using a height measuring device.

13. The system of claim 11, further comprising an indicating device, wherein the processor is further to:
    transmit a control signal associated with at least one of the start point or the end point to an indicating device, wherein the indicating device is to present at least one of the start point or the end point while taking the X-ray image.

14. The system of claim 11, wherein to determine, based on the reference data, at least one of the start point or the end point of the imaging region associated with the object, the processor is to:
    determine at least one of the start point or the end point of the imaging region based on the height data and a predetermined body part of the object.

15. The system of claim 13, further comprising a support for carrying the object, wherein the indicating device is movably installed on a support.

16. The system of claim 13, wherein the indicating device comprises a laser indicating device.

17. The system of claim 16, wherein the laser indicating device comprises an emitting unit and a receiving unit, the receiving unit synchronously moving with the emitting unit and being at a same height with the emitting unit.

18. A non-transitory computer readable medium, comprising executable instructions that, when executed by at least one processor, direct the at least one processor to perform a method, the method comprising:
- obtaining reference data associated with an object, the reference data comprising at least one of height data or historical data;
- determining, based on the reference data, at least one of a start point or an end point of an imaging region associated with the object;
- determining whether the start point or the end point needs to be modified;
- in response to determining that the start point or the end point needs to be modified, performing a simulated imaging based on the start point and the end point;
- determining, based on a simulation result, whether the start point or the end point satisfies a preset condition;
- determining a modified start point or a modified end point in response to determining that the start point or the end point does not satisfy the preset condition; and
- causing an acquisition device to take an X-ray image of the imaging region based on the start point and the end point, the start point and the modified end point, the modified start point and the end point, or the modified start point and the modified end point.

* * * * *